(12) United States Patent
Silver et al.

(10) Patent No.: US 10,729,900 B2
(45) Date of Patent: Aug. 4, 2020

(54) CONFIGURABLE ELECTRODES AND SENSORS

(71) Applicant: ZOLL Medical Corporation, Chelmsford, MA (US)

(72) Inventors: Annemarie Silver, Bedford, MA (US); Paolo Giacometti, Nashua, NH (US); Guy Johnson, Gloucester, MA (US); Gary Freeman, Waltham, MA (US); Lisa Campana, Waltham, MA (US); Frederick Geheb, Danvers, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 525 days.

(21) Appl. No.: 15/467,674

(22) Filed: Mar. 23, 2017

(65) Prior Publication Data
US 2017/0281925 A1    Oct. 5, 2017

Related U.S. Application Data

(60) Provisional application No. 62/314,797, filed on Mar. 29, 2016.

(51) Int. Cl.
*A61B 5/00* (2006.01)
*A61N 1/04* (2006.01)
*A61N 1/39* (2006.01)

(52) U.S. Cl.
CPC .......... *A61N 1/046* (2013.01); *A61B 5/4848* (2013.01); *A61B 5/6823* (2013.01); *A61B 5/6832* (2013.01); *A61B 5/6843* (2013.01); *A61N 1/0496* (2013.01); *A61N 1/3925* (2013.01); *A61B 2505/01* (2013.01); *A61B 2562/0219* (2013.01); *A61B 2562/0247* (2013.01)

(58) Field of Classification Search
CPC .... A61N 1/046; A61N 1/0492; A61N 1/0496; A61N 1/3904; A61N 1/3925; A61N 1/36014; A61B 5/1135; A61B 5/6823
See application file for complete search history.

(56) References Cited

U.S. PATENT DOCUMENTS

| 3,460,542 | A | | 8/1969 | Gemmer |
| 3,744,482 | A | | 7/1973 | Kaufman et al. |
| 3,826,245 | A | | 7/1974 | Funfstuck |
| 5,496,257 | A | * | 3/1996 | Kelly .................. A61H 31/005 600/454 |

(Continued)

FOREIGN PATENT DOCUMENTS

| DE | 2644236 C3 | 4/1981 |
| EP | 396048 A1 | 11/1990 |

(Continued)

*Primary Examiner* — Max F Hindenburg
(74) *Attorney, Agent, or Firm* — Finch & Maloney PLLC

(57) ABSTRACT

Example defibrillator electrode assemblies compression assemblies are described that may be dimensioned and configured for use on a patient despite physical constraints that limit the area or locations on a patient onto which an electrode assembly may be placed. A cardio pulmonary resuscitation (CPR) assembly is also described that protects a patient with a transthoracic incision from further injury during application of CPR compressions proximate to the incision.

24 Claims, 21 Drawing Sheets

(56) References Cited

U.S. PATENT DOCUMENTS

| | | | |
|---|---|---|---|
| 5,591,213 A * | 1/1997 | Morgan | A61N 1/3931 607/5 |
| 6,148,233 A | 11/2000 | Owen et al. | |
| 6,253,099 B1 | 6/2001 | Oskin et al. | |
| 6,306,107 B1 * | 10/2001 | Myklebust | A61B 5/1036 600/587 |
| 6,546,285 B1 | 4/2003 | Owen et al. | |
| 2003/0004547 A1 | 1/2003 | Owen et al. | |
| 2006/0211934 A1 | 9/2006 | Hassonjee et al. | |
| 2008/0200973 A1 * | 8/2008 | Mallozzi | A61N 1/046 607/142 |
| 2009/0076363 A1 | 3/2009 | Bly et al. | |
| 2010/0049266 A1 * | 2/2010 | Ochs | A61H 31/005 607/5 |
| 2010/0056881 A1 | 3/2010 | Libbus et al. | |
| 2010/0241181 A1 * | 9/2010 | Savage | A61N 1/046 607/5 |
| 2011/0022105 A9 | 1/2011 | Owen et al. | |
| 2011/0230925 A1 * | 9/2011 | Copp-Howland | A61N 1/046 607/8 |
| 2013/0104288 A1 * | 5/2013 | Schlottau | A41D 1/002 2/209.13 |
| 2013/0325096 A1 | 12/2013 | Dupelle et al. | |
| 2015/0320994 A1 * | 11/2015 | Buchanan | A61N 1/0492 607/142 |
| 2016/0136415 A1 * | 5/2016 | Bunch | A61N 1/0492 607/142 |

FOREIGN PATENT DOCUMENTS

| | | |
|---|---|---|
| EP | 1720446 B1 | 7/2010 |
| WO | 1998039061 A2 | 9/1998 |

\* cited by examiner

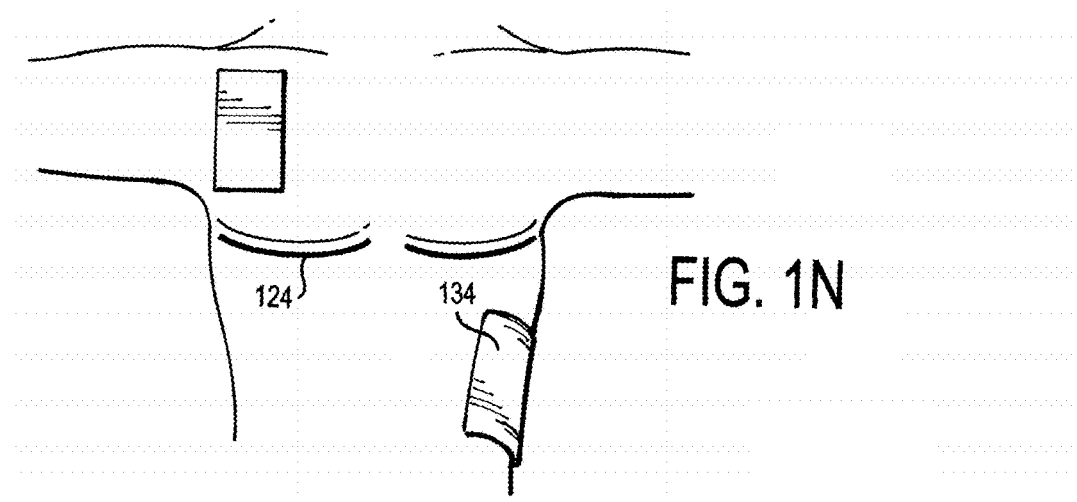
FIG. 1N
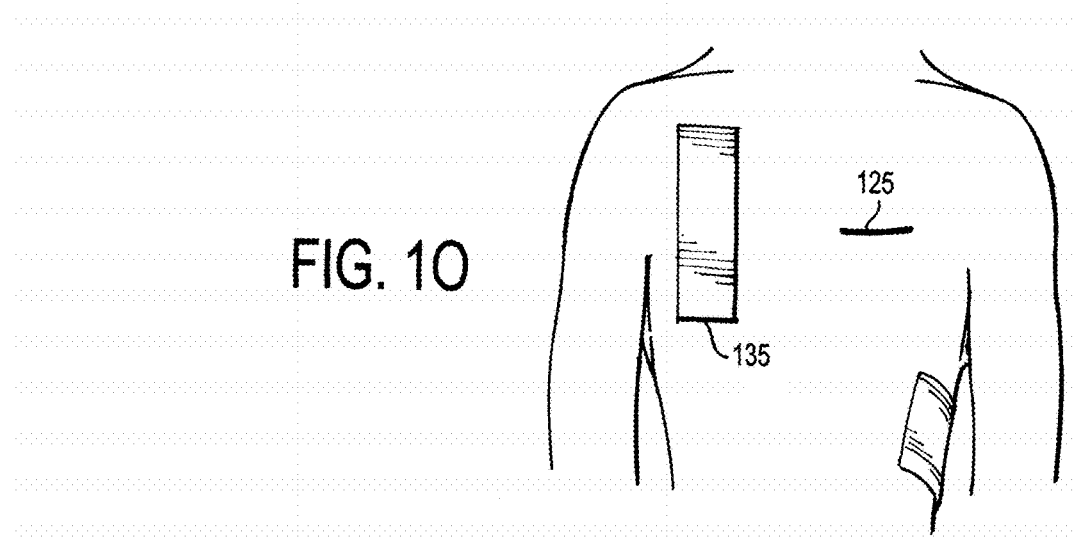
FIG. 1O
FIG. 1P
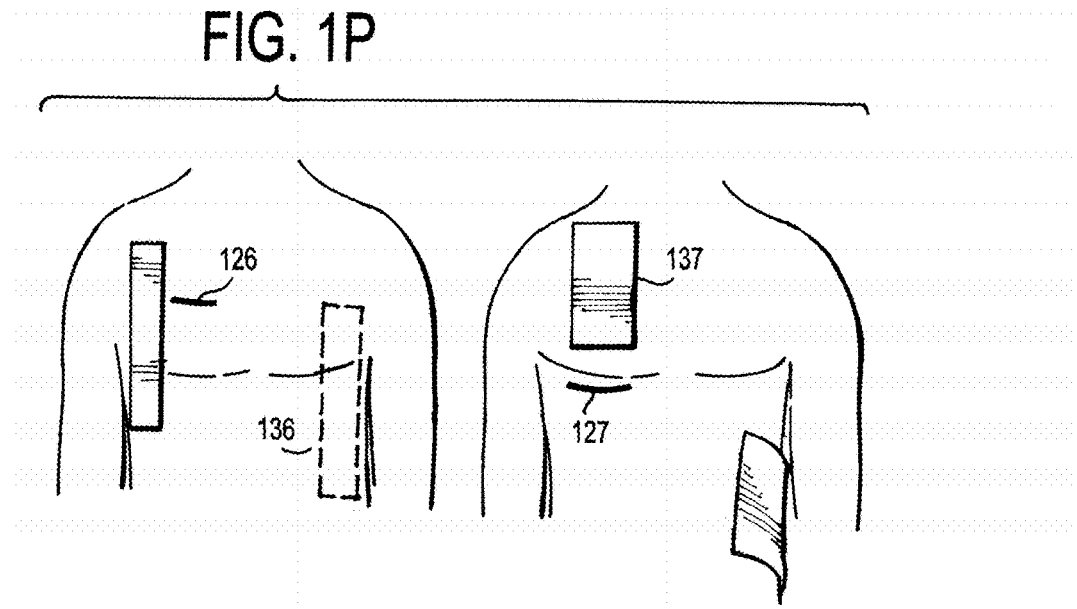

CONFIGURABLE ELECTRODES AND SENSORS

TECHNICAL FIELD

The present disclosure relates generally to cardiac resuscitation. Specifically, the present disclosure is related to medical equipment and procedures involved with cardiac resuscitation.

BACKGROUND

Defibrillators are used to treat Sudden Cardiac Arrest by applying a defibrillating shock to the heart of a cardiac arrest patient via electrodes placed on the chest of the patient. An electrocardiogram (ECG) signal of a patient experiencing cardiac arrest, properly measured and analyzed, provides an indication of whether the patient's heart is exhibiting a shockable rhythm or a non-shockable rhythm. A shockable rhythm refers to an aberrant ECG signal where a defibrillation shock is advised for restoration of a normal heartbeat, while a non-shockable rhythm refers to an ECG signal where a defibrillation shock is not advised. Ventricular fibrillation, for example, is a shockable rhythm, while asystole or pulseless electrical activity is an example of a non-shockable rhythm. Defibrillators are also capable of treating other dysrhythmias (irregular heartbeats), such as atrial fibrillation, bradycardia, and tachycardia. An ECG signal may be obtained through electrodes placed on the chest of the patient, and the defibrillating or cardioverting shock may be applied through the same electrodes.

During resuscitation, treatment protocols recommended by the American Heart Association and European Resuscitation Council advise for the rescuer to regularly check the patient's pulse or to evaluate the patient for signs of circulation. If no pulse or sign of circulation is present, the rescuer may be often instructed to perform cardio pulmonary resuscitation (CPR) on the victim for an appropriate period of time between shock analyses, where CPR involves applying both chest compressions and ventilations to the victim. Chest compressions and/or ventilations may be monitored during the course of CPR, for example, through systems and technologies that incorporate real-time CPR feedback (e.g., REAL CPR HELP® systems available from ZOLL® Medical Corporation) and which may implement resuscitation assemblies (e.g., CPR-D-PADZ® resuscitation assemblies, CPR STAT-PADZ® resuscitation assemblies, and OneStep CPR resuscitation assemblies available from ZOLL® Medical Corporation) having a sensor for obtaining chest compression related information for manual CPR providers. For example, ZOLL's CPR-D-PADZ® resuscitation assemblies and CPR STAT-PADZ® resuscitation assemblies include a pair of electrode pads and a single chest compression sensor.

SUMMARY

One example of a defibrillation electrode assembly for use in providing resuscitative treatment to a patient of the present disclosure includes a therapy pad. The therapy pad includes a non-conductive substrate and an electrically conductive layer in contact with the non-conductive substrate and configured to distribute a defibrillation current. A pattern is disposed on the therapy pad, the pattern depicting at least one boundary at which a first portion of the therapy pad is configured to be separable from a second portion of the therapy pad, the first portion and the second portion each including a portion of the electrically conductive layer. In one example of the defibrillation electrode assembly the pattern includes guidance for a user to separate the first portion from the second portion of the therapy pad. In one example of the defibrillation electrode assembly the pattern includes at least one line indicating a location along which the first portion and the second portion are separable from one another. The therapy pad also includes a perimeter edge, and further wherein the perimeter edge includes a curved edge from a point at the perimeter edge to an end of the at least one straight line to form a rounded corner. In one example of the defibrillation electrode assembly the pattern includes perforations defined by at least the non-conductive substrate and the electrically conductive layer. In one example of the defibrillation electrode assembly the pattern includes a plurality of indentations in at least the non-conductive substrate and the electrically conductive layer. In one example of the defibrillation electrode assembly the pattern includes at least one polygon. In some examples, the at least one polygon includes a first polygon disposed within a second polygon. In some examples, the first polygon has a generally rectangular shape having an approximate aspect ratio of at least 3:1 and the second polygon has a rectangular shape having an approximate aspect ratio of at least 3:1. In one example of the defibrillation electrode assembly the pattern includes a plurality of approximately parallel lines defining a plurality of elongated members. In one example of the defibrillation electrode assembly the first portion of the therapy pad and the second portion of the therapy pad are both electrically connected to a power source. In some examples, the first portion of the therapy pad and the second portion of the therapy pad are electrically connected to each other by a conductor after being separated. In some examples, the first portion of the therapy pad and the second portion of the therapy pad each are approximately rectangular in shape and have an aspect ratio of greater than 1:1. In some examples, the aspect ratio greater than 1:1 is at least 2:1. In some examples, the conductor connecting the first portion of the therapy pad and the second portion of the therapy pad is approximately 10 cm long, permitting separation of the first portion and the second portion of less than approximately 10 cm. In one example, the defibrillation electrode assembly further includes a protective mask between the pattern and the electrically conductive layer, the non-conductive, protective mask defining a minimum size of the first portion of the therapy pad. In one example, the defibrillation electrode assembly further includes an adhering material in contact with the electrically conductive layer. In some examples the adhering material includes a conductive gel. In one example, the defibrillation electrode assembly further includes an adhering material configured to transmit the defibrillation current from the electrically conductive layer to the patient and configured to couple the therapy pad to a sensitive region of the patient, wherein the adhering material exhibits a peel strength of between 0.01 pounds (lbs) and 0.5 lbs at a pull rate of 10 inches/min. In one example of the defibrillation electrode assembly the therapy pad has an aspect ratio of greater than 3:1. In one example the defibrillation electrode assembly further includes a sterile pouch configured to hold a chest compression sensor within a sterile space.

One example of a defibrillation electrode assembly for use in providing resuscitative treatment to a patient of the present disclosure includes at least one therapy pad. The at least one therapy pad includes a non-conductive substrate and an electrically conductive layer in contact with the non-conductive substrate and configured to distribute a defibrillation current, wherein the at least one therapy pad has an aspect ratio of greater than 3:1. In one example, the aspect ratio of the at least one therapy pad is at least 3:1. In one example, the aspect ratio of the at least one therapy pad is at least 5:1. In one example, the at least one therapy pad includes an approximately rectangular shaped therapy pad having an aspect ratio of at least 3:1. In one example, the at least one therapy pad further includes a perimeter edge, and further wherein the perimeter edge has a curved edge from a point at the perimeter edge to an end of the at least one straight line to form a rounded corner. In one example, the at least one therapy pad further includes a pattern disposed on the at least one therapy pad, the pattern depicting at least one boundary at which a first portion of the at least one therapy pad is configured to be separable from a second portion of the at least one therapy pad, the first portion and the second portion each including a portion of the electrically conductive layer. In some examples, the pattern includes a plurality of approximately parallel lines defining a plurality of elongated members. In some examples, the pattern includes perforations defined by at least the non-conductive substrate and the electrically conductive layer. One example of the defibrillation electrode assembly further includes an adhering material configured to transmit the defibrillation current from the electrically conductive layer to the patient and configured to couple the therapy pad to a sensitive region of the patient, wherein the adhering material exhibits a peel strength of between 0.01 lbs and 0.5 lbs at a pull rate of 10 inches/min. One example of the defibrillation electrode assembly further includes a sterile pouch configured to hold a chest compression sensor within a sterile space.

One example of a defibrillation electrode assembly for use in providing resuscitative treatment to a patient of the present disclosure includes at least one therapy pad and a sterile pouch configured to hold a chest compression sensor within a sterile space. In examples, the therapy pad includes a non-conductive substrate, and an electrically conductive layer in contact with the non-conductive substrate and configured to distribute a defibrillation current. In one example, the defibrillation electrode assembly further includes a chest compression sensor wherein the chest compression sensor comprises at least one of an accelerometer and a gyroscope. In examples, the chest compression sensor is configured to be placed at a position away from the sternum during administration of chest compressions. In examples, the chest compression sensor is configured to be placed over the sternum during administration of chest compressions. In examples, the sterile pouch is configured to prevent exposure of the chest compression sensor within a sterile field associated with a transthoracic incision. In one example, the defibrillation electrode assembly further includes an adhering material in contact with the electrically conductive layer. In examples the adhering material comprises a conductive gel. In examples, the chest compression sensor is removably coupled to the therapy pad by an adhesive. In one example, the defibrillation electrode assembly further includes a wrist band attached to the chest compression sensor. In examples, the defibrillation electrode assembly further includes an electrical conductor connected to the chest compression sensor, the electrical conductor configured to transmit at least one of acceleration data and orientation data from the CPR sensor to a processor. In examples, the sterile pouch is configured to encapsulate the chest compression sensor and at least a portion of the electrical conductor. In examples, the electrical conductor comprises a ribbon cable. In examples, the defibrillation electrode assembly further includes a pattern disposed on the therapy pad, the pattern depicting at least one boundary at which a first portion of the therapy pad is separable from a second portion of therapy pad, the first portion and the second portion each including a portion of the electrically conductive layer. In examples, the sterile pouch includes a sealed closure for maintaining the chest compression sensor within the sterile space. In examples, the opening of the sealed closure exposes the chest compression sensor to a surrounding environment. In examples, the defibrillation electrode assembly further includes a pattern disposed on the therapy pad, the pattern depicting at least one boundary at which a first portion of the therapy pad is configured to be separable from a second portion of the therapy pad, the first portion and the second portion each including a portion of the electrically conductive layer. In examples, the therapy pad has an aspect ratio of greater than 3:1. In examples, the defibrillation electrode assembly further includes an adhering material configured to transmit the defibrillation current from the electrically conductive layer to the patient and configured to couple the therapy pad to a sensitive region of the patient, wherein the adhering material exhibits a peel strength of between 0.01 lbs and 0.5 lbs at a pull rate of 10 inches/min.

One example of a chest compression assembly used to provide resuscitative treatment to a patient having a sensitive region includes a first portion configured to come into contact with the patient on a first side of a sensitive region, a second portion configured to come into contact with the patient on a second side of the sensitive region, the first side and the second side being on opposite sides of the sensitive region, a central portion configured to be located over the sensitive region, a chest compression sensor coupled to at least one of the first portion, the second portion and the central portion, wherein the chest compression assembly is configured to alleviate pressure on the sensitive region by distributing force applied from chest compressions over the sensitive region to the first side and the second side of the sensitive region. In one example, the central portion has a length greater than a width of the sensitive region. In one example, the first portion and the second portion each have a spiral conformation in which a radius of the spiral conformation is a continuous function of a polar angle. In one example, the chest compression assembly further includes a user side configured to receive the CPR chest compressions and a thorax side configured to confront the thorax. In one example, the chest compression assembly further includes a resilient pad disposed on the thorax side configured for diffusing pressure applied to the thorax by the manual CPR compressions. In one example, the chest compression sensor is coupled to at least one of the first portion and the second portion. In one example, the sensitive region comprises a surgical incision. In one example, the chest compression assembly further includes a first hinge connecting the central portion to the first portion and a second hinge connecting the central portion to the second portion.

One example of a method for using a defibrillation electrode assembly to provide resuscitative treatment to a patient includes receiving the electrode assembly including a therapy pad and a pattern disposed on the therapy pad, the pattern depicting at least one boundary at which a first portion of the therapy pad is configured to be separable from a second portion of the therapy pad, the first portion and the second portion each including a portion of an electrically conductive layer, removing the first portion of the therapy pad from the second portion of the therapy pad, and applying the first portion of the therapy pad to the patient and not applying the second portion of the therapy pad to the patient.

In one example, the first portion is applied to a child. In one example, the first portion is applied to an adult. In one example, the first portion is applied to a post-surgical patient at locations away from a sensitive region of the patient. In one example, the first portion is applied to a post-sternotomy patient at locations away from a transthoracic line. In one example, the first portion is applied to a patient having a plurality of electrocardiography electrodes placed thereon at locations away from the electrocardiography electrodes.

One example of a method for using a sensor assembly to provide resuscitative treatment to a patient includes receiving the sensor assembly including a covering material surrounding at least a portion of a chest compression sensor, the covering material having a pattern depicting at least one boundary at which a first portion of the covering material is configured to be separable from a second portion of the covering material, the first portion of the covering material surrounding at least a portion of the chest compression sensor, removing the first portion of the covering material from the second portion of the covering material, and applying the first portion of the covering material to the patient and not applying the second portion of the covering material to the patient. In one example, the first portion is applied to a child. In one example, the first portion is applied to an adult. In one example, the first portion is applied to a post-surgical patient at locations away from a sensitive region of the patient. In one example, the first portion is applied to a sternum of the patient.

One example of a method for using a defibrillation electrode assembly to provide resuscitative treatment to a patient includes receiving the sensor assembly including a covering material surrounding at least a portion of a chest compression sensor, the covering material having a pattern depicting at least one boundary at which a first portion of the covering material is configured to be separable from a second portion of the covering material, the first portion of the covering material surrounding at least a portion of the chest compression sensor, removing the first portion of the covering material from the second portion of the covering material, and applying the first portion of the covering material to the patient and not applying the second portion of the covering material to the patient. In one example, the first portion is applied to a child. In one example, the first portion is applied to an adult. In one example, the first portion is applied to a post-surgical patient at locations away from a sensitive region of the patient. In one example, the first portion is applied to a post-surgical patient at a sensitive region of the patient. In one example, the first portion is applied to a sternum of the patient.

One example of a method for using a defibrillation electrode assembly to provide resuscitative treatment to a patient includes receiving the defibrillation electrode assembly including a first therapy pad and a second therapy pad, each of the therapy pads including an electrically conductive layer having a first side and a second side longer than the first side, and applying the first therapy pad and the second therapy pad to the patient so that each of the second sides are aligned substantially parallel with respect to one another. In one example, the first and second therapy pads are applied to the patient so as to avoid a sensitive region of the patient. In one example, the sensitive region includes a transthoracic incision. In one example, the first and second therapy pads are applied to the patient so as to avoid a plurality of electrocardiography electrodes placed on the patient. In one example, the method further includes removing a chest compression sensor removably attached to the defibrillation electrode assembly and placing the chest compression sensor within a sterile field proximate to a transthoracic incision. The method further includes removing the chest compression sensor from a sterile pouch.

An example of a method for using a chest compression assembly to provide resuscitative treatment to a patient having a sensitive region includes placing a first portion of the chest compression assembly on a body of the patient on a first side of the sensitive region, placing a second portion of the chest compression assembly on the body of the patient on a second side of the sensitive region, the first side and the second side being on opposite sides of the sensitive region, and applying a downward compressive force to a central portion of the chest compression assembly, the first portion and the second portion of the chest compression assembly transferring the downward compressive force from the central portion of the chest compression assembly to the body of the patient on the first and second sides of the sensitive region. The method further includes disposing at least one chest compression sensor on at least one of the first portion and the second portion proximate to a patient thorax. In examples, the method further includes attaching a resilient pad to the central portion, the resilient pad protecting the sensitive region of the patient from direct application of force from the central portion. In examples, the sensitive region of the patient comprises a surgical incision.

An example of a method for using a defibrillation electrode assembly to provide resuscitative treatment to a patient, the defibrillation electrode assembly having a sterile pouch configured to hold a chest compression sensor within a sterile space includes removing the chest compression sensor from the sterile pouch, placing the chest compression sensor within a sterile field of the patient, and using the chest compression sensor to monitor chest compressions performed on the patient. In examples, the chest compression sensor is placed on the sternum of the patient. In examples, the chest compression sensor is placed at a location away from the sternum of the patient. In examples, the method further includes detaching the chest compression sensor from the defibrillation electrode assembly. In examples, the method further includes placing the defibrillation electrode assembly within the sterile field of the patient. In examples, the method further includes removing at least one perimeter portion from a placement pad of the chest compression sensor.

An example of a therapy pad of a defibrillation electrode assembly for use in providing resuscitative treatment to a patient includes a non-conductive substrate, an electrically conductive layer in contact with the non-conductive substrate and configured to distribute a defibrillation current, and an adhering material configured to transmit the defibrillation current from the electrically conductive layer to the patient and configured to couple the therapy pad to a sensitive region of the patient, wherein the adhering material exhibits a peel strength of between 0.01 lbs and 0.5 lbs at a pull rate of 10 inches/min. In examples, the adhering material exhibits a peel strength of less than 0.4 lbs at a pull rate of 10 inches/min. In examples, the adhering material exhibits a peel strength of less than 0.3 lbs at a pull rate of 10 inches/min. In examples, the adhering material exhibits a peel strength of less than 0.2 lbs at a pull rate of 10 inches/min. In examples, the adhering material exhibits a peel strength of less than 0.1 lbs at a pull rate of 10 inches/min. In examples, the defibrillation electrode assembly further includes a pattern disposed on the therapy pad, the pattern depicting at least one boundary at which a first portion of the therapy pad is configured to be separable from a second portion of the therapy pad, the first portion and the second portion each including a portion of the electrically conductive layer. In examples, the therapy pad has an aspect ratio of greater than 3:1. In examples, the defibrillation electrode assembly further includes a sterile pouch configured to hold a chest compression sensor within a sterile space.

An example of a sensor assembly for use in providing resuscitative treatment to a patient includes a chest compression sensor configured to provide motion information for characterizing chest compressions and an adhering material configured to couple the chest compression sensor to a sensitive region of the patient, wherein the adhering material exhibits a peel strength of between 0.01 lbs and 0.5 lbs at a pull rate of 10 inches/min. Some examples of the sensory assembly further include a covering material surrounding at least a portion of the chest compression sensor, the covering material having a pattern depicting at least one boundary at which a first portion of the covering material is configured to be separable from a second portion of the covering material, the first portion of the covering material surrounding at least a portion of the chest compression sensor. Some examples of the sensory assembly further include a sterile pouch configured to hold the chest compression sensor within a sterile space.

An example of a sensor assembly for use in providing resuscitative treatment to a patient includes a chest compression sensor configured to provide motion information for characterizing chest compressions and a covering material surrounding at least a portion of the chest compression sensor, the covering material having a pattern depicting at least one boundary at which a first portion of the covering material is configured to be separable from a second portion of the covering material, the first portion of the covering material surrounding at least a portion of the chest compression sensor. In examples, the sensor assembly further includes a low peel strength adhering material on a portion of the covering material. In examples, the pattern depicting at least one boundary is molded in the covering material. In examples, the sensor assembly further includes an adhering material configured to couple the chest compression sensor to a sensitive region of the patient, wherein the adhering material exhibits a peel strength of between 0.01 lbs and 0.5 lbs at a pull rate of 10 inches/min.

BRIEF DESCRIPTION OF THE DRAWINGS

FIGS. 1K-1P are illustrations of various thoracic incisions shown in FIGS. 1A-1F and around which have been placed defibrillator electrode assemblies, in examples.

Figure 1A:
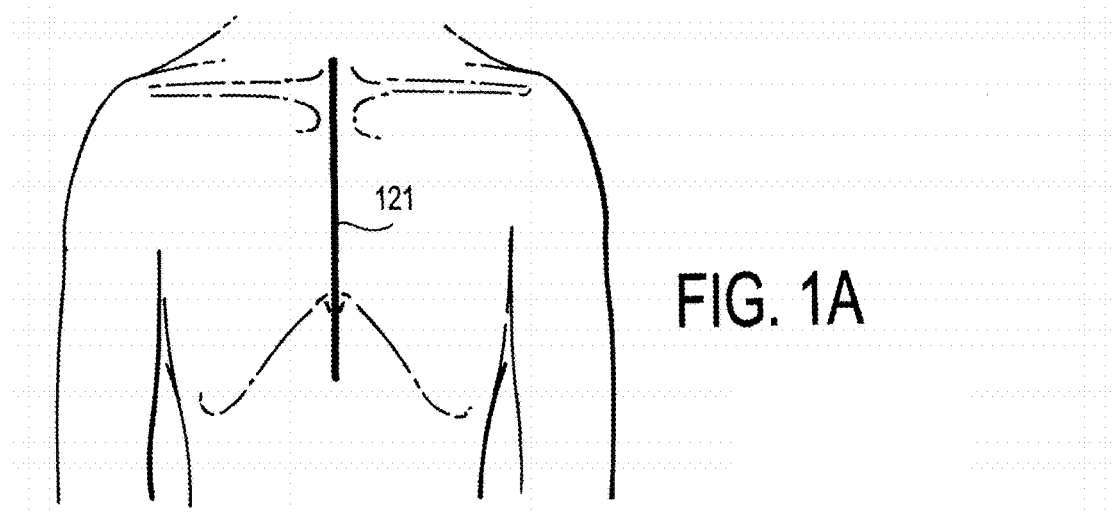
FIGS. 1A-1F are illustrations of an anterior of a patient having various thoracic incisions.

The figures depict various examples of the present disclosure for purposes of illustration only. Numerous variations, configurations, and other examples will be apparent from the following detailed discussion.

DETAILED DESCRIPTION

The present disclosure relates to various examples of configurable electrodes and sensor assemblies, such as defibrillator electrode assemblies and chest compression assemblies and other medical equipment used to resuscitate patients. These example electrodes and sensor assemblies may be adjustable in size and/or shape, dimensioned and/or configured for use on a patient in a manner that accounts for physical constraints that limit the areas or locations on a patient onto which an electrode assembly, sensor and/or a chest compression assembly may be placed. For example, a thorax of a patient requiring resuscitation or defibrillation may already be occupied by various other medical devices (e.g., electrodes of a 12-lead system), thus inhibiting timely placement of a defibrillation electrode assembly or chest sensor assembly in a situation where time is of the essence. In another example, a patient with a small thorax (e.g., an infant or a young child) may not have a thorax large enough to accommodate a defibrillator electrode assembly or chest compression sensor assembly that is sized for an adult body. In another example, a patient with a transthoracic incision (i.e., a post-sternotomy patient) may be further injured by chest compressions as the pressure applied by the compressions to the thorax of the patient weakens (or even re-opens) the incision. Incisions, including but not limited to a transthoracic incision, also reduce the area available for electrodes and sensor assemblies due to the sterile field that must be maintained around the incision. The adhesive material commonly found on electrode pad assemblies or sensor assemblies may be so strong that it may have a tendency to further injure sensitive regions, such as along surgical lines or incisions. For example, the adhesive may tend to re-open wounds or surgical lines, exacerbating the injury. Accordingly, in some examples, electrodes and/or sensors described herein may employ a relatively weak adhesive material, having a low peel strength. Applying an electrode or sensor that mechanically couples to the patient, yet is not strongly adhesive, would not cause further injury to sensitive regions of a patient.

Some of the examples described herein include configurable electrodes and sensor assemblies, such as defibrillator electrode assemblies ("electrode assemblies" herein for brevity) that can be dimensioned and configured to fit on thoraxes that have limited space in which to place an electrode assembly, or chest compression sensor assemblies that can be dimensioned and configured to be placed on or near the sternum of the patient in a compact manner. One example of an electrode assembly of the present disclosure includes a pattern disposed on a therapy pad of an electrode assembly that depicts at least one boundary along which portions of the therapy pad can be separated. This enables a shape of an electrode assembly to be configured to correspond to at least one of the size and shape of area on a thorax of a patient that is available to receive the electrode assembly. Benefits of this example include the ability to size and appropriately place electrode assemblies on patients of different sizes, on thoraxes with limited exposed area (due to other medical devices occupying thorax space), and on patients having wounds (e.g., transthoracic incisions) that should be treated carefully to either avoid further injury of the wound or to avoid invading a sterile field surrounding the wound. An example of a sensor assembly of the present disclosure may include a covering material encapsulating or otherwise surrounding a chest compression sensor where the covering material may similarly have a pattern depicting one or more boundaries along which portions of the covering material may be separated. This also enables the size and shape of the sensor assembly to be configured so as to be placed on or near the sternum of the patient in a desirable manner, for subsequently monitoring applied chest compressions. In this example, the configurability of size and shape of the sensor assembly may allow for the sensor assembly to be used for patients of different sizes, on thoraxes with limited exposed area, and on patients having wounds.

One example of a configurable electrode of the present disclosure includes high aspect ratio electrode assemblies that are long and narrow and can thus be placed in areas of a thorax otherwise not accessible to conventionally shaped electrode assemblies. In various embodiments, the electrode assembly may include a therapy pad having an aspect ratio of greater than 3:1, greater than 4:1, greater than 5:1, greater than 6:1, greater than 7:1, greater than 8:1, greater than 9:1, greater than 10:1, up to 20:1 or even greater. In addition to the benefits presented above, also applicable to this example, a further benefit of this example is providing electrode assemblies that, when used, provide a substantially uniform distribution of electrical energy through the body and heart of the patient. This reduces the risk of burning the patient and improves the likelihood of properly stimulating the heart of the patient.

In other embodiments of the present disclosure, an electrode and/or sensor assembly may have an adhering material configured to couple with a sensitive region (e.g., surgical line, wound/burn area, scar tissue, sutured region) of a patient so as to exhibit a relatively low peel strength (e.g., for a 10 inch/minute pull rate, less than 0.5 lbs, less than 0.4 lbs, less than 0.3 lbs, less than 0.2 lbs, less than 0.1 lbs, less than 0.05 lbs, less than 0.01 lbs, greater than 0.01 lbs) at the sensitive region. In an example, a therapy pad of an electrode assembly may include an electrically conductive layer for distributing a defibrillation current and an adhering material that transmits the defibrillation current from the electrically conductive layer. The adhering material may also be configured to couple the therapy pad to the sensitive region of the patient, yet may be weakly adherent to the sensitive region, for example, having a low peel strength. Similarly, in another example, a sensor assembly may include a chest compression sensor configured to provide motion information in characterizing chest compressions. The sensor assembly may further include an adhering material configured to couple the chest compression sensor to the sensitive region of the patient, yet may be easily removable from the sensitive region.

One example of a configurable electrode and/or sensor assembly of the present disclosure includes a sterile pouch removably coupled to a therapy pad of the electrode assembly. The sterile pouch is configured to store a sterile chest compression sensor prior to use so that the chest compression sensor (and, optionally, a portion of an attached lead wire connecting the chest compression sensor to a controller) may be used within a sterile field (e.g., of a transthoracic incision) while still maintaining the sterility of the field. Hence, both the chest compression sensor and the wire/cable connecting the sensor to a controller may remain sterile before, during and after application of chest compressions. One benefit is a reduction in the risk of infection of a thoracic wound or incision that can otherwise increase when placing a chest compression sensor within the sterile field. Furthermore, using the sterile pouch enables the chest compression sensor to optionally be placed within the sterile field proactively and prior to a cardiac event requiring chest compression without compromising the sterile field. In various embodiments, other parts of the resuscitation assembly may be sterile. For example, an electrode assembly may be sterile, allowing for parts, or the entirety, of the electrode assembly to be placed within the sterile field, as desired.

One example of a sensor of the present disclosure includes a chest compression assembly configured to distribute the force applied from a manual chest compression to opposing sides of a transthoracic incision. Distributing the forces of the chest compressions using the chest compression assembly protects the patient from further injury or re-opening of the transthoracic incision during application of chest compressions. Or, such force distribution may even have beneficial effects in keeping the transthoracic incision closed. One benefit of this is improved recuperation time of a patient and preservation of the integrity of the incision even in the event of the application of chest compressions.

In some examples, the configurable chest compression sensor may be enclosed or contained within a sterile pouch so that placement of the chest compression sensor within a sterile field surrounding a wound or incision does not compromise the sterility of the sterile field.

Configurable Electrode Assemblies

Figure 1B:
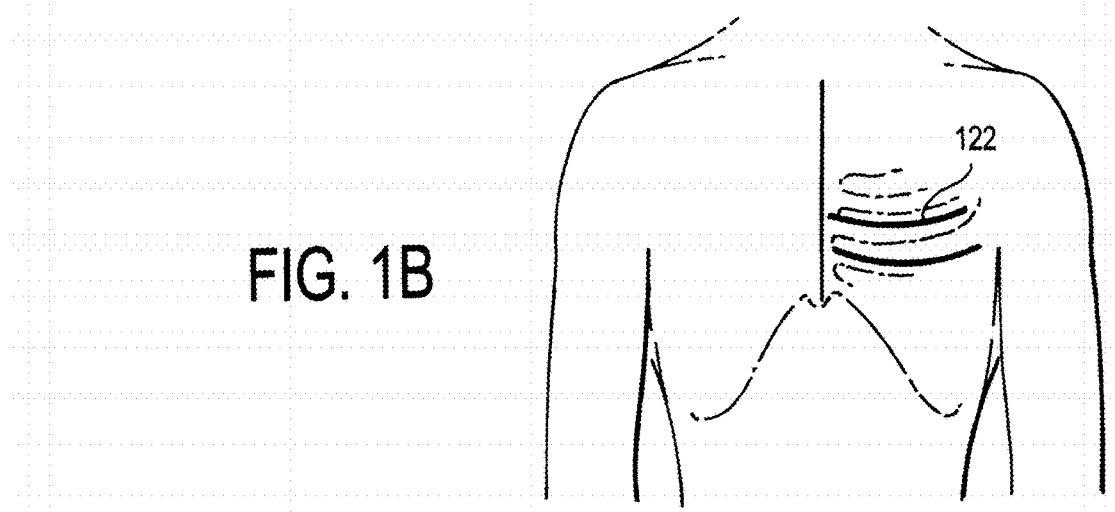
Figure 1C:
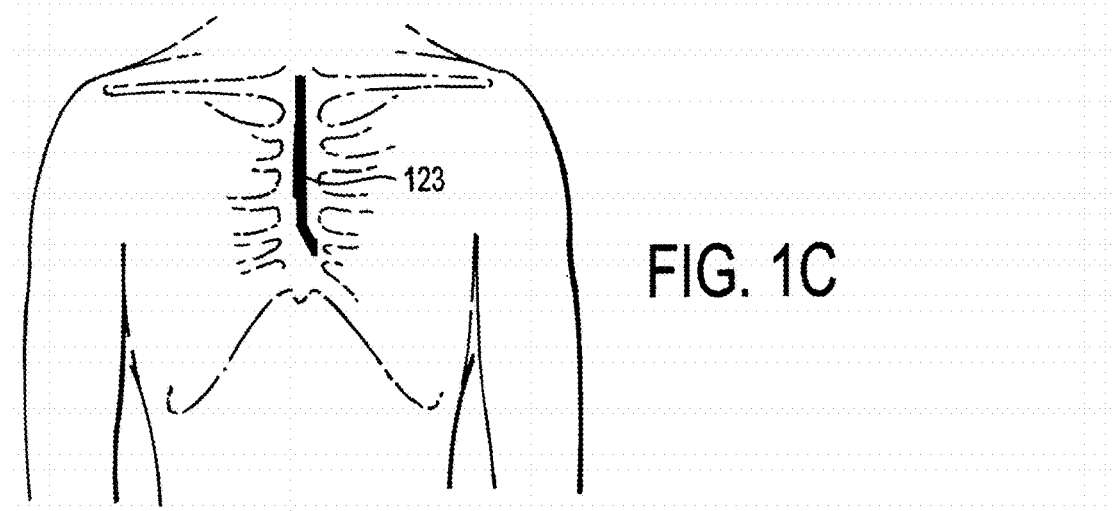
Figure 1D:
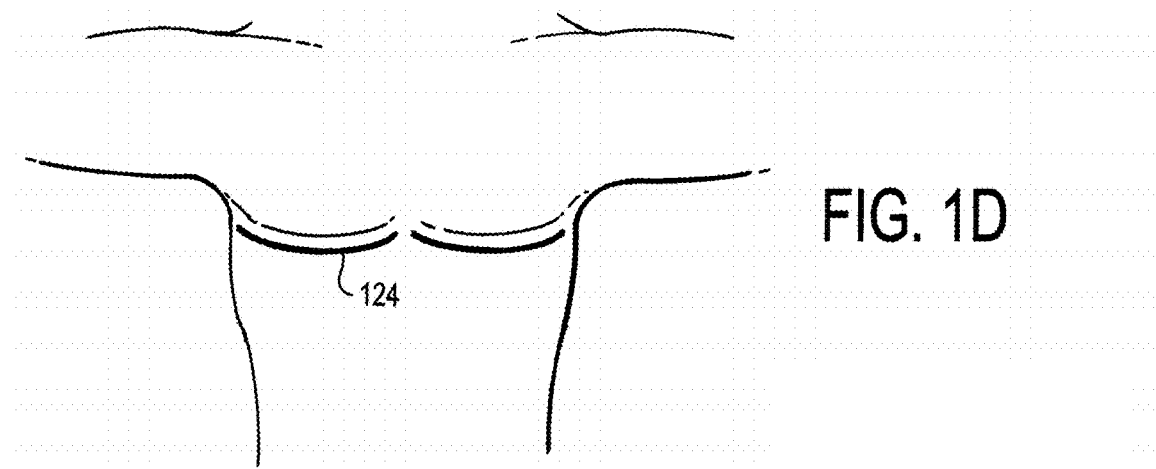
Figure 1E:
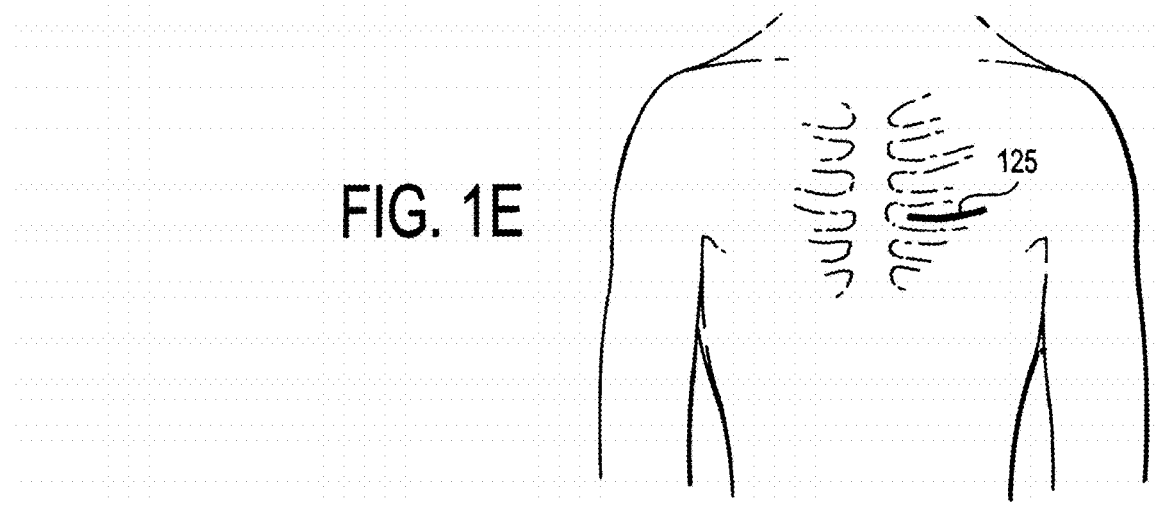
Figure 1F:
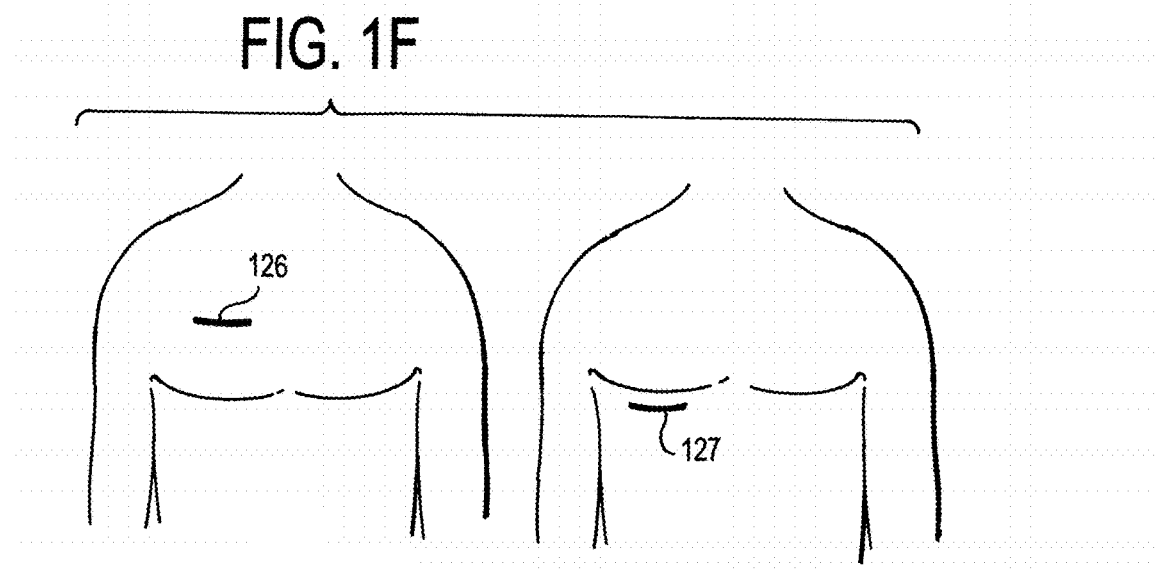

As indicated above, examples of the present disclosure include configurable electrode assemblies that may be dimensioned and configured for use on a patient despite physical constraints that limit the areas or locations on a patient onto which an electrode assembly can be placed. Example situations in which these electrode assemblies may be beneficially used are those in which a thorax of a patient is already occupied by medical devices or sensors, or the patient has a small thorax (like an infant or small child). For convenience of illustration, FIGS. 1A-1F show various thoracic incisions in which examples of the present disclosure may be used and illustrate the challenge of placing a pad, such as a defibrillator pad or a chest compression sensor, on an incised thorax of a patient. FIG. 1A shows a thorax with a transthoracic incision 121. FIG. 1B shows a thorax with a lateral thoracotomy incisions 122. FIG. 1C shows a thorax with a hemisternotomy incision 123. FIG. 1D shows a thorax with bilateral thorascosternotomy incisions 124. FIG. 1E shows an incision minimally invasive and/or robotic surgeries such as an incision 125 for heart valve surgery. FIG. 1F shows an incision 126 for minimally invasive aortic valve surgery and an incision 127 for minimally invasive mitral and intracuspid valve surgery. Examples described below are applicable to any of these situations and other incisions not shown.

The incision itself and an area of tissue adjacent to the incision may be referred to herein as a "sensitive region." The sensitive region can be a regular or irregular region extending from one centimeter to several centimeters from the incision. A sensitive region may also include other areas of tissue that are particularly susceptible to injury and/or aggravation. For example, in addition to an incision, the sensitive region may include a wound, infection, scar or other similarly vulnerable type of area of the body.

Figure 1G:
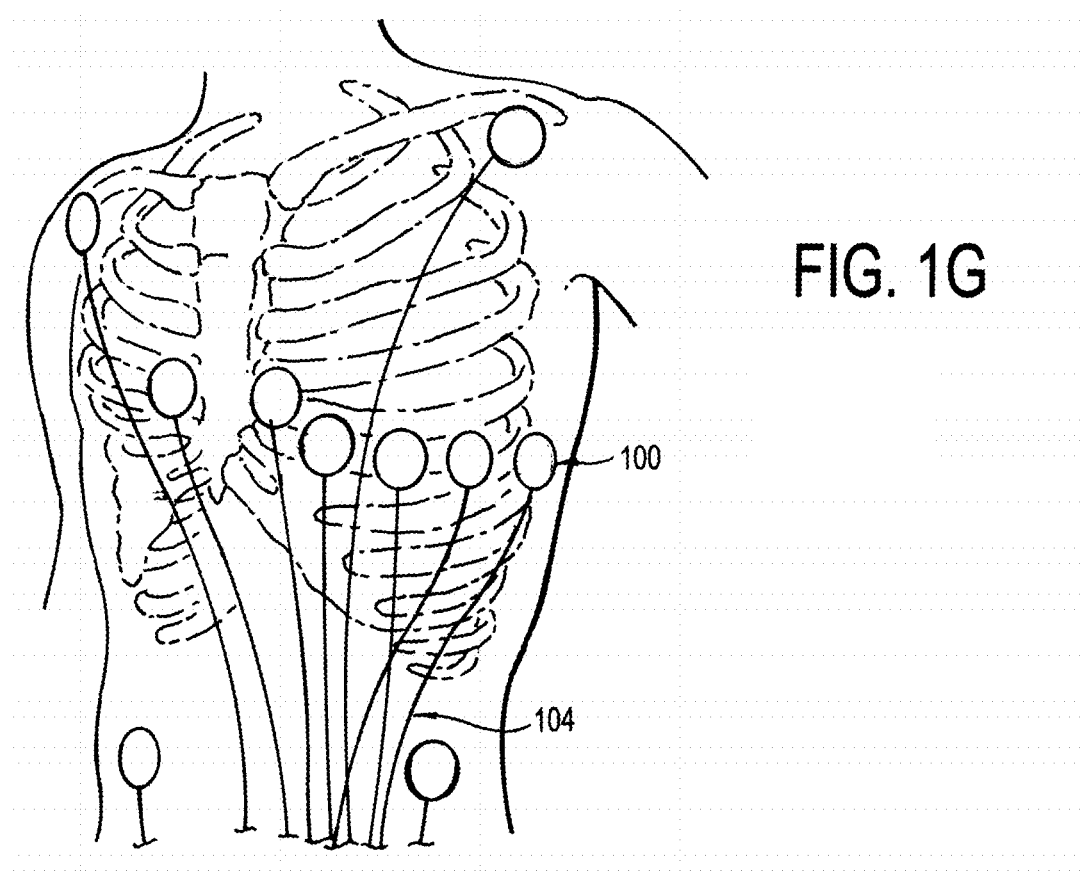
FIG. 1G is an illustration showing conventional electrodes of a 12 lead electrode system placed on a thorax of an adult patient, in an example.
Figure 1H:
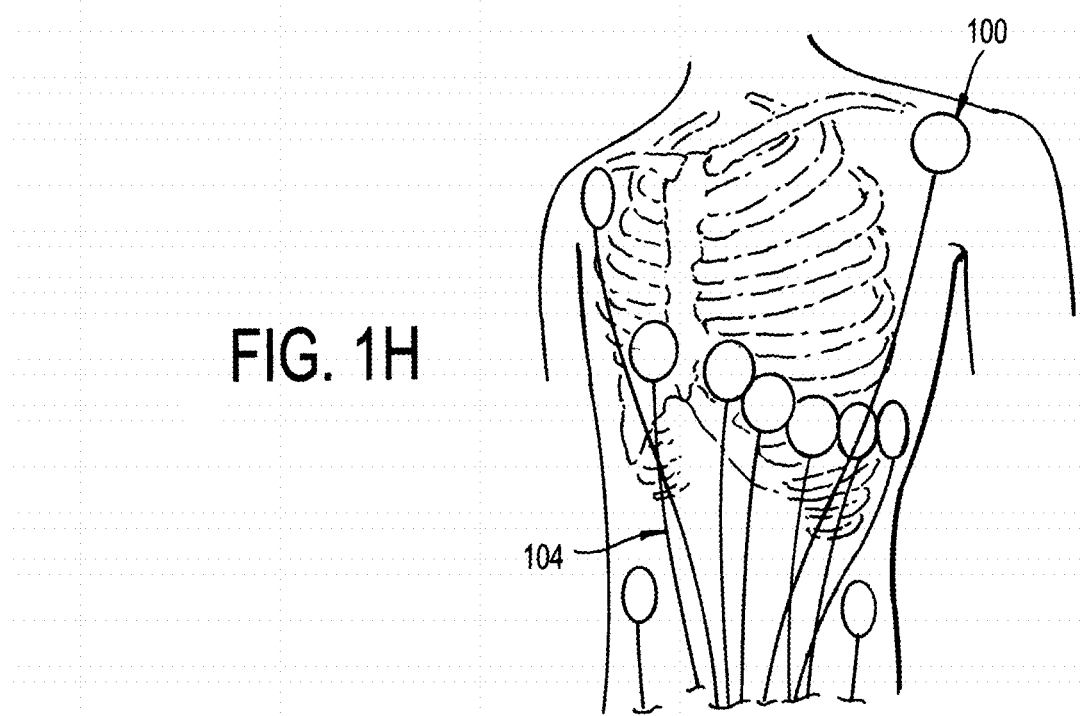
FIG. 1H is an illustration showing conventional electrodes of a 12 lead electrode system placed on a thorax of a child patient, in an example.

FIG. 1G illustrates, for comparison with FIG. 1H, an adult thorax onto which electrodes of a 12 lead electrode system (each of which is identified according to its location on the thorax with a standard identifier of V1-V6, RA, LA, RL, or LL), collectively 100, have been placed. Each of the electrodes 100 is connected to a corresponding data cable, collectively, 104. The 12 lead electrode system is used to monitor the electrical characteristics of a beating heart from various locations on the thorax. As is shown in FIG. 1G, despite the numerous electrodes 100 and corresponding data cables 104, area on the adult thorax remains available for the placement of additional electrode assemblies or other medical devices.

However, the placement of defibrillator electrode assemblies is more difficult for a patient with a small thorax because there is less room available on the thorax on which to place electrodes (or other medical devices). For example, FIG. 1H shows conventionally sized electrodes 100 and data cables 104 of a 12 lead electrode system on the smaller thorax of a child. As is apparent upon inspection of FIG. 1H, a higher proportion of available thorax area for a small thorax is occupied by the conventionally sized electrodes 100 and data cables 104. This makes placement of defibrillator electrode assemblies (or other medical devices) more difficult because there is less available area in which to place them. These spatial constraints can cause delays in placing defibrillator electrode assemblies (or other medical devices) and/or suboptimal placement locations for these medical devices in situations in which time is of the essence. These spatial constraints can also increase the risk of a health care practitioner removing one or more medical devices (including, but not limited to one or more of the conventionally sized electrodes 100) from the small thorax, thereby reducing the collection of monitoring data, disrupting the operation of another medical device, or otherwise complicating treatment for a patient in extremis.

Figure 1I:
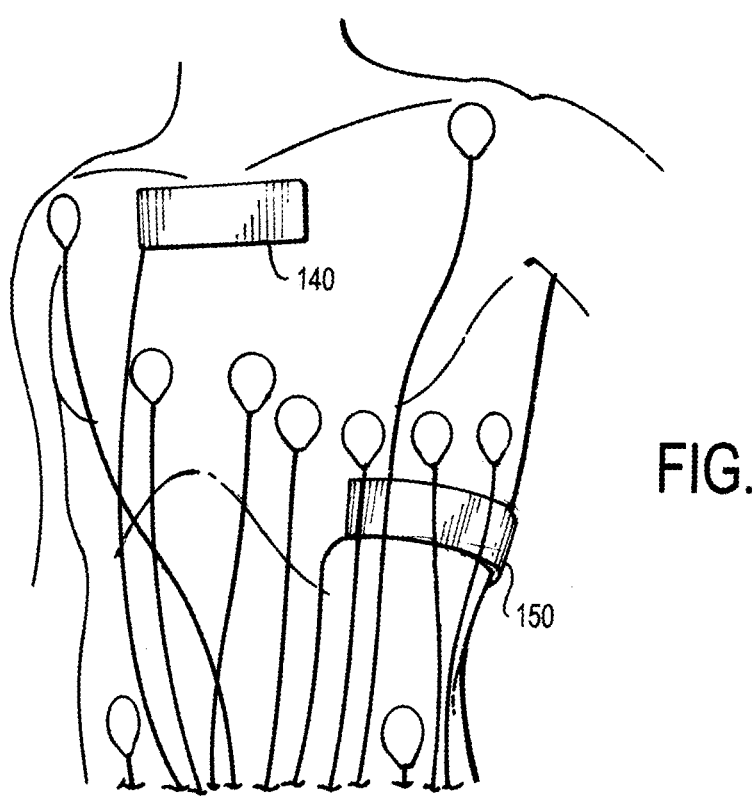
FIG. 1I is an illustration showing defibrillator electrode assemblies having configurable size and shape used in combination with a 12 lead electrode system placed on a thorax of an adult patient, in an example.
Figure 1J:
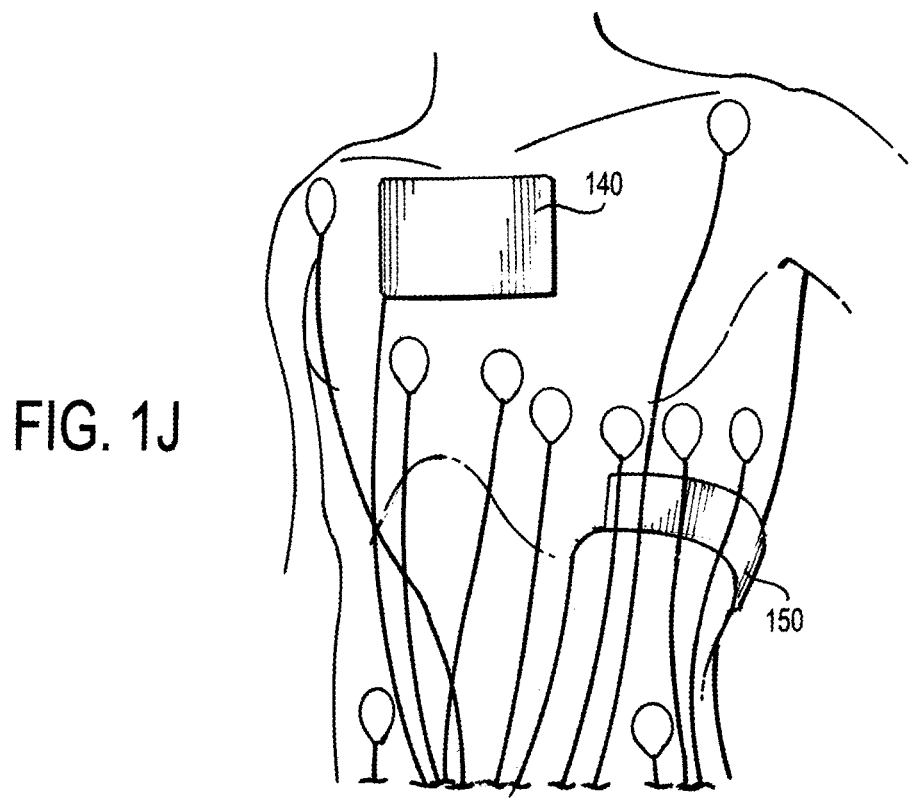
FIG. 1J is an illustration showing defibrillator electrode assemblies having configurable size and shape used in combination with a 12 lead electrode system placed on a thorax of an adult patient, in an example.
Figure 1K:
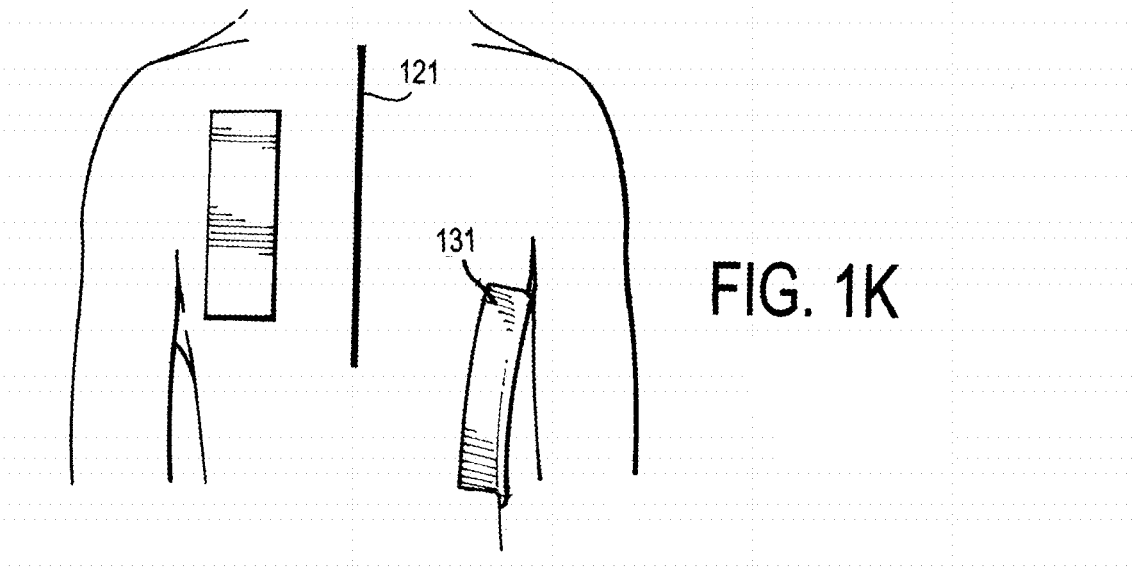
Figure 1L:
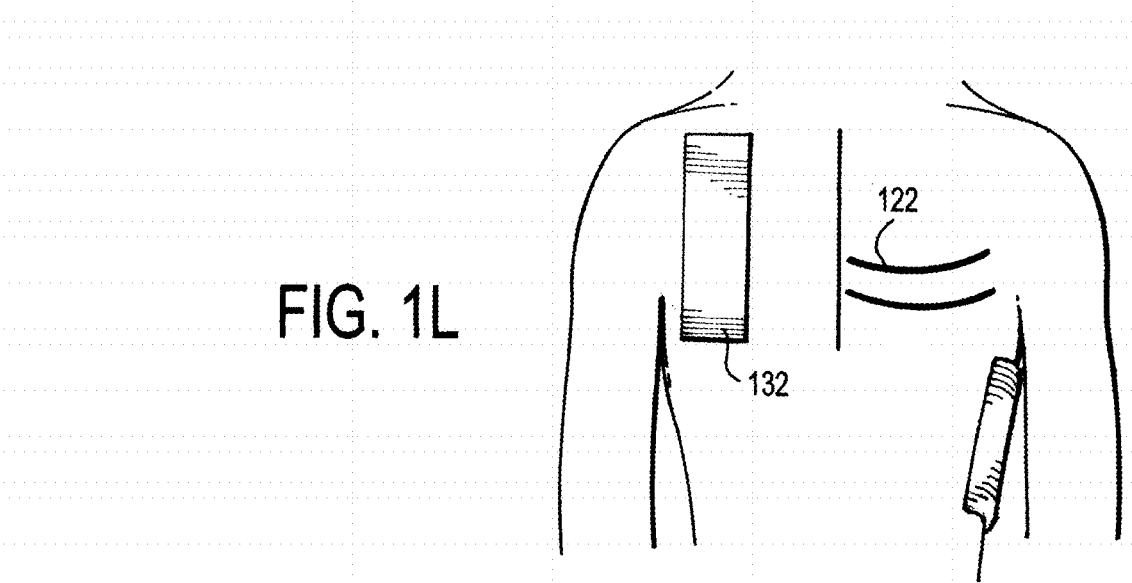

As schematically shown in FIG. 1I, example configurable electrode assemblies of the present disclosure enable more convenient placement on thoraxes of any size, including those having surface area already substantially occupied by other medical equipment, without the drawbacks indicated above. As shown in FIG. 1I, configurable defibrillator electrode assemblies 140 and 150 can be dimensioned and configured based on, among other factors, area available on a thorax not already occupied by medical equipment. For instance, the electrode assemblies 140 and 150 are strategically shaped and placed so as not to interfere with the 12-lead electrode system, yet still be able to provide an electrical path through the heart for defibrillation. In particular, the elongated shape of the electrode assembly 150 allows for compact placement adjacent to the V1-V6 electrodes of the 12-lead system. As shown, the electrode assembly 140 is placed on the upper right chest of the patient and the electrode assembly 150 is placed on the side of the lower left thorax of the patient. An alternative configuration of configurable defibrillator electrode assemblies 140 and 150 is shown in FIG. 1J in which configurable defibrillator electrode assembly 140 has a different aspect ratio than configurable defibrillator electrode assembly 150.

Figure 1M:
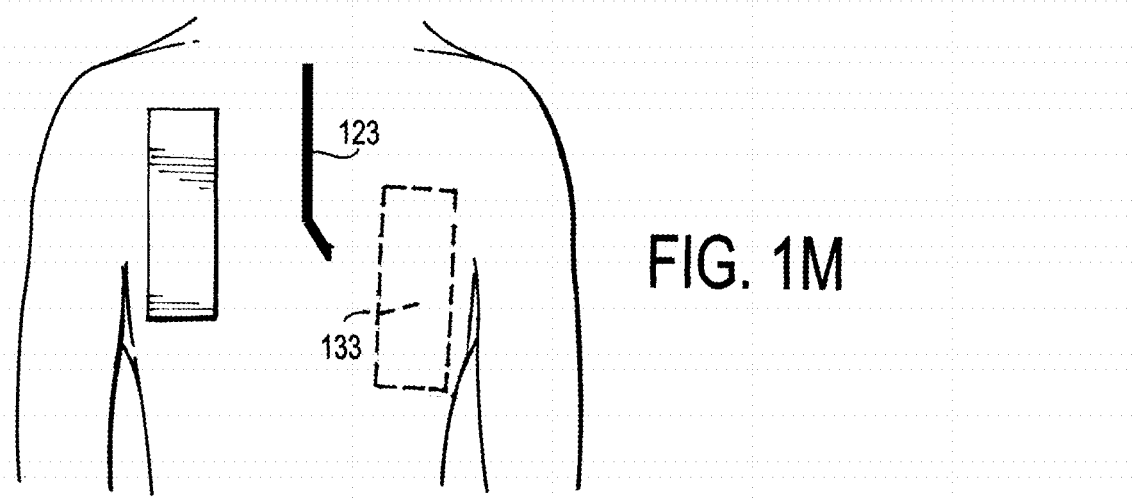

FIGS. 1K to 1P illustrate thoraxes with the incisions 121, 122, 123, 124, 125, 126, and 127 previously shown in FIGS. 1A-1F that now also have configurable defibrillator electrode assemblies 131, 132, 133, 134, 135, 136, and 137, respectively, of the present disclosure also placed on the thorax. FIGS. 1K, 1L, 1N and 1O show the electrode assemblies 131, 134 placed on the lower left side of the thorax of the patient and the electrode assemblies 132, 135 placed on the upper right chest of the patient. FIG. 1M and one example of FIG. 1P each include one defibrillator electrode assembly (133 and 136, respectively) disposed on a posterior (back) of the patient, represented by a dashed outline. FIG. 1M and one example of FIG. 1P each include one defibrillator electrode assembly (133 and 136, respectively) disposed on a posterior (back) of the patient, represented by a dashed outline. The individual configurable defibrillator electrode assemblies 131, 132, 133, 134, 135, 136, and 137 have a high aspect ratio (as will be described below in more detail) and are oriented parallel to one another. While this can improve the effectiveness of defibrillation, neither high aspect ratio electrode assemblies nor parallel orientation are required for examples described herein. Furthermore, as is shown in FIGS. 1K to 1P, the configurable defibrillator electrode assemblies 131, 132, 133, 134, 135, 136, and 137 are applied to avoid a sensitive region surrounding of the corresponding incision 121, 122, 123, 124, 125, 126, and 127.

Figure 1Q:
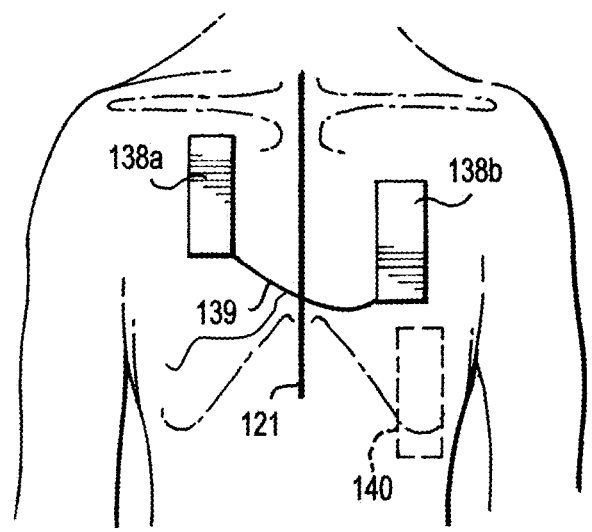
FIG. 1Q is an illustration of two anterior defibrillator electrode assemblies electrically connected to one another after being placed on a patient on opposite sides of an incision and one posterior defibrillator electrode assembly also placed on a patient, in an example.

FIG. 1Q is an illustration of two anterior defibrillator electrode assemblies 138a and 138b electrically connected to one another via conductor 139. These two anterior defibrillator assemblies 138a and 138b are placed on either side of a transthoracic incision 121 on a patient, thus avoiding the sensitive area. Examples of the defibrillator electrode assemblies 138a and 138b include the one depicted FIG. 4. Example defibrillator electrode assemblies shown in FIG. 5 and FIG. 6 may also be used. For instance, the electrode assemblies 138a and 138b may be initially attached to one another, similar to that shown in FIGS. 4 and 5. When in use, as shown, the electrode assemblies 138a and 138b may be separated from one another and placed on the anterior of the patient so as to avoid the sensitive region(s) (e.g., surgical lines, wounds). FIG. 1Q also shows a defibrillator electrode assembly also placed on the posterior of the patient. Because the separate parts of the electrode assemblies 138a and 138b on the anterior of the patient remain electrically connected, the defibrillation current may still travel between the anterior and the posterior of the patient (through the heart) in a suitable manner. That is, the defibrillation current travels from the electrode assemblies 138a, 138b placed on the anterior of the patient to the electrode assembly 140 placed on the posterior of the patient, or vice versa. Also, as discussed further below, because the electrode assemblies 138a, 138b are separated from one another, the current distribution through the body will differ accordingly.

Figure 1R:
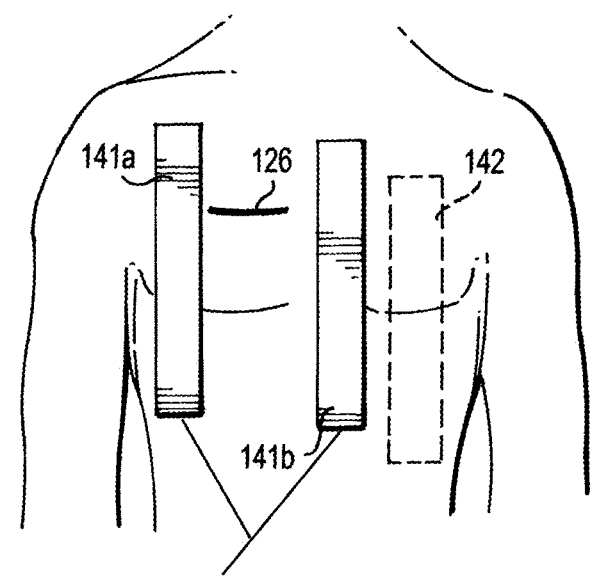
FIG. 1R is an illustration of two anterior defibrillator electrode assemblies electrically connected to one another after being placed on a patient on opposite sides of an incision and one posterior defibrillator electrode assembly also placed on a patient, in an example.

FIG. 1R is similar to FIG. 1Q in that it depicts two anterior defibrillator electrode assemblies 141a and 141b on opposite sides of an incision 126 with a posterior defibrillator electrode assembly 142, in avoidance of the sensitive region. The anterior defibrillator electrode assemblies 141a and 141b may be electrically connected to one another, similar to the example shown in FIG. 1Q so that defibrillation current may travel from the anterior electrode assemblies 141a and 141b, through the heart, to the posterior electrode assembly 142, or vice versa.

Figure 2A:
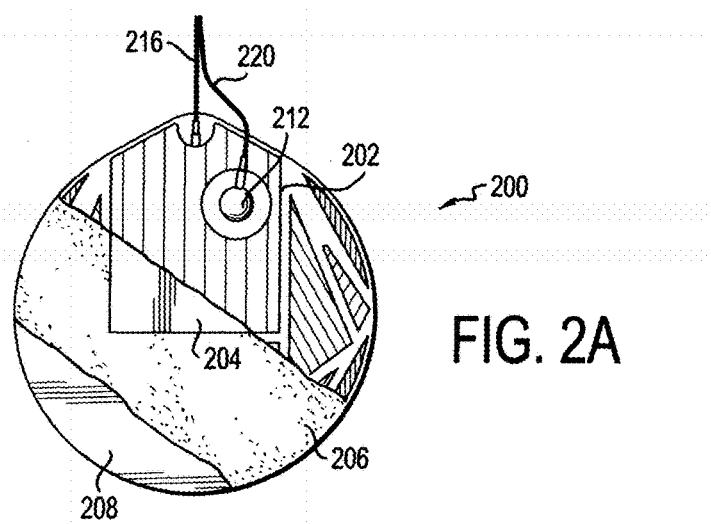
FIG. 2A is a plan schematic view of a configurable electrode assembly showing selectively exposed layers of the electrode assembly, in an example.
Figure 2B:
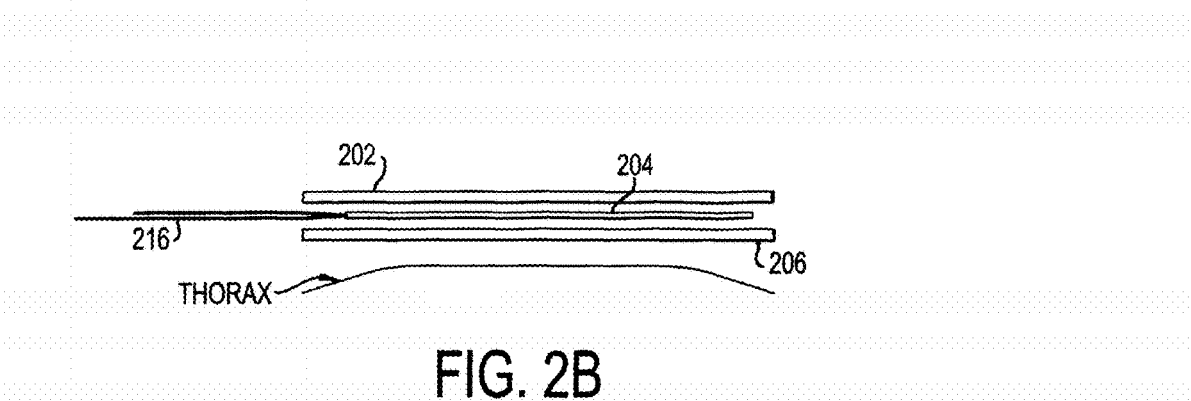
FIG. 2B is a cross-sectional view of the configurable electrode assembly of FIG. 2A, in an example.
Figure 2C:
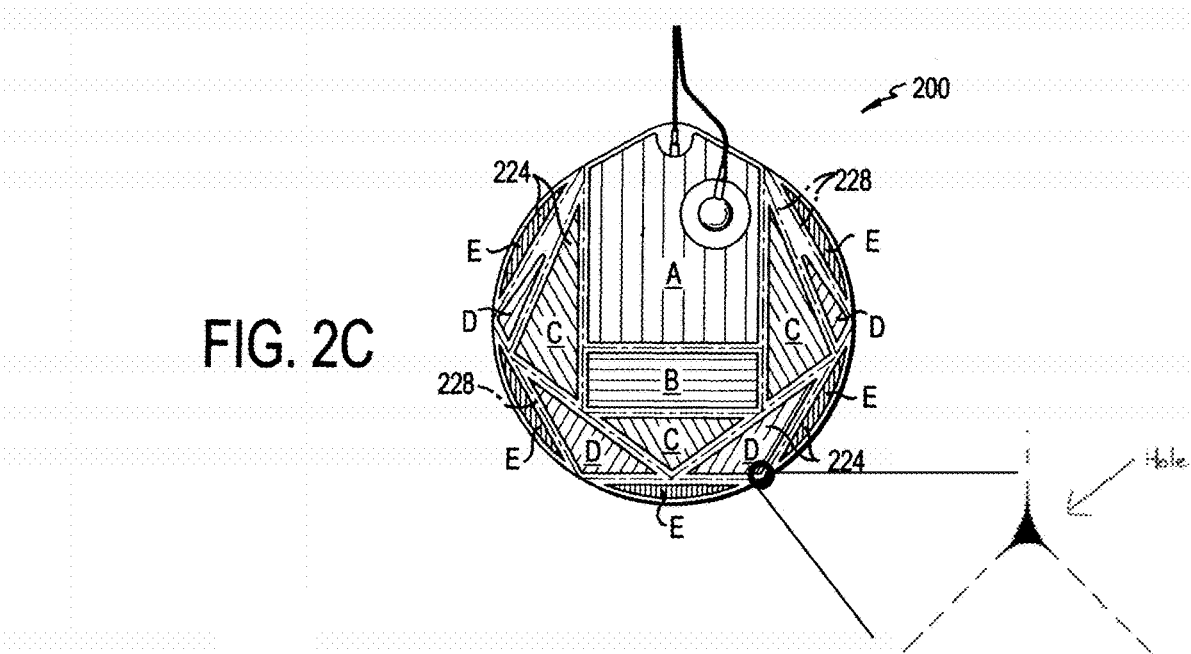
FIG. 2C is a plan view of a configurable electrode assembly that includes a pattern for configuring the electrode assembly into any of a variety of shapes and sizes, in an example.

An example configurable electrode assembly 200 is shown in FIGS. 2A, 2B, and 2C. FIGS. 2A and 2B illustrate various layers of the example configurable electrode assembly 200. FIG. 2C illustrates an example pattern disposed on a layer of the example configurable electrode assembly 200 that can be used to dimension and configure the example configurable electrode assembly 200 to a size corresponding to a Broselow scale color.

The layers of the example configurable electrode assembly 200 shown in FIGS. 2A and 2B include an image layer 202, an electrically conductive layer 204, an adhesive layer 206, and a release layer 208. The image layer 202 in the example of FIGS. 2A and 2B is shown as a top layer over the electrically conductive layer 204, the adhesive layer 206, and the release layer 208. In some embodiments, the image layer 202 also acts as a non-conductive substrate for supporting the electrically conductive layer 204 and adhesive layer 206. In this example, the image layer 202 depicts a pattern (described below in more detail in the context of FIG. 2C) that is used to size and configure the electrode assembly 200 (and more specifically in some examples, the conductive layer 204). In some embodiments, the pattern may be used to size and configure the electrode assembly according to the Broselow scale. However, it can be appreciated that the image layer 202 is not required to correspond to the Broselow scale, as any other configuration for appropriately adjusting to the size or shape of the electrode may be employed. The pattern provided by the image layer may be used to adjust the size and/or shape configuration of the electrode so as to provide a suitable range of defibrillation energies corresponding to appropriate characteristics (e.g., age, weight, height) of the patient. For example, a larger electrode may be preferable for a larger patient (e.g., adult), to provide a sufficient energy level of defibrillation current. Similarly, a smaller electrode may be preferable for a smaller patient (e.g., child), to provide a comparatively lower energy level of defibrillation current. Accordingly, the amount of energy provided to the patient may be adjusted, in part, by removing a portion of the electrode(s), resulting in smaller sized electrode(s).

In this example configurable electrode assembly 200, the image layer 202 is disposed on a side of the electrically conductive layer 204 opposite the adhesive layer 206. When in this configuration, the image layer 202 serves as an electrically non-conductive substrate onto which the various other layers of the electrode assembly 200 are attached, either directly or indirectly. In some examples, this electrically non-conductive substrate is referred to as a non-therapy side. Alternatively, the image layer 202 may be disposed at another location with the configurable electrode assembly 200. For example, the image layer 202 may be printed on any one or more of the electrically conductive layer 204, the adhesive layer 206, or the release layer 208. In examples, an electrically non-conductive substrate separate from the image layer 202 is used as a non-therapy substrate.

In examples, the image layer 202 may be deposited as a layer of ink or pigment on or within one of the other layers of the example configurable electrode assembly 200. In other examples, the image layer 202 is stamped or embossed into one of the other layers of the example configurable electrode assembly 200. These examples are merely presented for illustration. It will be understood that other methods may be used to provide a pattern on a configurable electrode assembly.

In some examples, the configurable electrode assembly 200 may also include a protective mask that prevents removal of portions of the example configurable electrode assembly 200 that would otherwise reduce it below a minimum size needed for effective and/or safe operation. In other examples, the protective mask covers areas not corresponding to a pattern of boundaries. This prevents removal of any portions not intended to be separable. Examples of protective masks include Kevlar, polycarbonate, or other tough materials that resist cutting or tearing. In some examples, the protective mask is separate from the image layer 202 but in other examples the protective mask is part of the image layer 202. The protective mask is adaptable to any of the embodiments described herein that include portions separable from one another (e.g., as shown in FIGS. 2A, 2B and 2C, 3, 4, 5, 6, 9A and 9B, 11B and 11C, among other embodiments within the scope of the present disclosure and not shown).

The electrically conductive layer 204 is a flexible layer comprising an electrical conductor. Examples of electrical conductors used for the electrically conductive layer 204 include, for example copper, tin, silver, silver chloride, any other suitable conductive material, and alloys thereof. In some embodiments, the electrically conductive layer 204 includes a conductive ink that may be printed thereon. The electrically conductive layer 204 transmits energy from a defibrillator controller (that includes a power source) to the patient in the event that the defibrillator controller is actuated. In an example, the electrically conductive layer 204 also includes a conductive electrolyte gel such as a hydrogel (not shown) that is at least coextensive with the electrically conductive layer 204. Disposing the conductive electrolyte gel on a therapy side of the electrode assembly between the electrically conductive layer 204 and a patient facilitates the effective transfer of electrical energy to the patient.

In the example shown in FIGS. 2A and 2B, the electrically conductive layer 204 has a length and a width each corresponding to a minimum electrode area used for electrically conductive layers 204. This minimum electrode area is used to set a lower limit on current density flowing from the electrically conductive layer 204 into the patient during defibrillation to reduce of risk and/or severity of burns to the patient. While the electrically conductive layer 204 shown in FIG. 2A is shown as having a square-type shape, the electrically conductive layer 204 can be any shape. In another example, the electrically conductive layer 204 is coextensive with the boundaries of the example configurable electrode assembly 200. In another example, the electrically conductive layer 204 is nearly coextensive with the boundaries of the example configurable electrode assembly 200 except for a non-conductive border between an outer perimeter of the electrically conductive layer 204 and an outer perimeter of the example configurable electrode assembly 200 as a whole. This non-conductive border can help prevent an unintentional transfer of charge to a healthcare practitioner accidentally handling or touching the example configurable electrode assembly 200 during actuation of the defibrillator controller.

An adhesive layer 206 is disposed on one side of the electrically conductive layer 204 and is used to securely, but temporarily, attach the example configurable electrode assembly 200 to a patient (in some cases to a sensitive region) and to transmit defibrillation current from the electrically conductive layer 204 to the patient. The adhesive layer 206, for example a hypoallergenic medical grade acrylic adhesive designed for use on human skin, is used to affix the example configurable electrode assembly 200 to a location on a patient. Using the adhesive layer 206 enables application of electrical energy to a desired location on the patient without any manual force being applied by a healthcare practitioner, thus improving the effectiveness of defibrillation and safety.

In some examples, the adhesive layer 206 is provided as a low peel strength adhering material. A low peel strength adhering material may enable secure placement and/or coupling of the configurable electrode assembly 200 to the patient during resuscitation and may be configured such that the electrode assembly is easily removable, without aggravating the area upon which it was previously adhered. Accordingly, the peel force applied to an incision during removal of the configurable electrode assembly 200 is relatively low, despite being able to (weakly) couple the electrode to the (sensitive) region of interest. Examples of low peel strength adhering materials have average values of from 0.001 lbs to 0.5 lbs when subject to a pull rate of 10 inches/min, and more specifically any one or more of from 0.001 lbs to 0.01 lbs, from 0.01 lbs to 0.1 lbs, from 0.01 lbs to 0.2 lbs, from 0.01 lbs to 0.3 lbs, from 0.01 lbs to 0.4 lbs, from 0.1 lbs to 0.2 lbs, from 0.1 lbs to 0.3 lbs, from 0.1 lbs to 0.4 lbs, from 0.2 lbs to 0.3 lbs, from 0.3 lbs to 0.5 lbs, from 0.3 lbs to 0.45 lbs. This reduces the risk of unintentionally re-opening or exacerbating an incision when removing the configurable electrode assembly 200. As discussed further herein, the low peel strength adhering material may be employed for resuscitation electrodes and sensors.

Peel strength of an adhering material can be measured by first placing the adhering material on a substrate (whether a paper sheet, a polymer sheet, a conductive material; as part of an electrode or sensor assembly). In examples, the substrate is approximately one inch wide by approximately several inches long. The substrate is then attached to a glass slide via the adhering material through a 1"×¼" window. That is, if the substrate is larger than 1"×¼", then a window liner is provided between the adhering material and the glass slide such that the area of coupling between the adhering material and the glass slide is limited to a 1"×¼" window. The substrate, adhering material, and glass slide are pressed together via a weight (e.g., 4.5 lb weight), and then coupled to a 90° peel test machine having a force gauge, where the machine moves the substrate in a direction perpendicular to the glass slide at a constant rate and angle (in this case 90°), while measuring the force required to remove the substrate from the glass slide. For peel strength values provided herein, the load application pull rate is 10 inches per minute. A portion of the substrate is attached to a portion of the test machine that will peel the substrate and adhering material from the glass slide at the selected load application pull rate. The test is operated for approximately five seconds, during which time the 90° peel test machine measures the force required to peel the substrate and adhering material from the glass slide. A suitable peel test machine may include a calibrated Chatillon DFIS (e.g., 2 or 10 pound unit), Chatillon DFS-050, or other machine having a force gauge with appropriate sensitivity.

Low peel strength adhering materials may also be applied to examples of chest compressions sensors described below.

Any suitable low peel strength adhering material may be employed. Low peel strength adhering materials may include, for example, silicone (e.g., medical grade silicone), adhesives used for wound/burn dressings, polymer, elastomer, rubber, acrylate, weak pressure sensitive adhesives, gel, soft silicone gel adhesives, hydrogel, electrically conductive gel, foam, padding or any other appropriate material that may be suitable to mechanically couple the electrode or sensor to a sensitive region of the patient, yet is also easily removable with low risk of causing further injury to the sensitive region.

The conductive layer 204 (and optionally the electrically conductive gel) and the adhesive layer 206 can be collectively referred to as a "therapy pad." In other examples, other layers may also be included in the definition of the therapy pad.

A release layer 208 is optionally (and temporarily) in contact with the adhesive layer 206. The release layer 208 is a protective film which prevents the adhesive layer 206 from unintentional adhesion to a surface prior to application to a patient and preserves the adhesiveness of the adhesive layer 206. Examples of release layer 208 include polymeric or paper sheets that may optionally be coated with a low surface energy substance to facilitate removal of the release layer 208 from the adhesive layer 206.

Also shown on the example configurable electrode assembly 200 is a chest compression sensor 212 that is releasably attached to the example configurable electrode assembly 200 for optional application to the patient. The chest compression sensor 212 is discussed below in more detail in the context of different examples. Lead wires 216 (which can be ribbon cables or some other electrical conductor) connect the electrically conductive layer 204 to a defibrillation controller (not shown) and optionally transmit signals to the defibrillation controller for the monitoring of the heartbeat of a patient prior to, during, and after electrical energy is applied to the patient.

The example configurable electrode assembly 200 shown in FIG. 2C includes a plurality of fields 224 and a plurality of boundaries 228. In this example, these fields 224 and boundaries 228 depict a pattern formed on, within, or as the image layer 202 of the example configurable electrode assembly 200. Much like markings on a measuring cup, the pattern of fields 224 and boundaries 228 on the example configurable electrode assembly 200 in FIG. 2A are used to provide guidance to a user when configuring a size or shape of an electrode. That is, a first portion of the configurable electrode assembly 200 can be removed (e.g., cut, torn, peeled, etc.) from the configurable electrode assembly 200 and not applied to the patient, while a second portion is applied to the patient. Hence, the boundaries may provide guidance to a user for how portions of the electrode assembly may be removed therefrom, resulting in an electrode having a different size and shape. The adjusted configuration may be preferable, for example, in the case of a smaller person, such as a child patient. In the example shown, the various sizes correspond to a particular height and/or weight of a pediatric patient indicated by the Broselow scale.

The Broselow scale is an internationally recognized standard color coding scheme used to administer various therapies to pediatric patients in appropriate doses. Upon presentation, a pediatric emergency patient is measured using a measuring tape that is color coded for various height ranges of the patient. Upon measuring the height of the patient and identifying a corresponding color using this "Broselow Tape," the color is then used to select, for example, a correspondingly color coded level of defibrillator energy. It will be appreciated that the Broselow scale is used only for illustration in this example. Various encoding schemes can be used in the image layer, including for patient classes of any one or more of height, weight, and age categories, and/or based on ranges of energy to be applied to a patient during defibrillation.

The plurality of fields 224 includes individual fields 224A-E, each of which is separated by a boundary 228. In the example configurable electrode assembly 200 shown in FIGS. 2A, 2B, and 2C, the pattern includes straight line boundaries 228 along which some of the various fields 224 can be separated from one another. In some examples, the boundaries 228 may also correspond to perforations defined by one or more of the layers of the example configurable electrode assembly 200, thus improving the convenience by which portions of the example configurable electrode assembly 200 can be separated from one another. For example perforations may be formed in the non-conductive image layer 202 and/or the electrically conductive layer 204. Alternatively, rather than perforations, the boundary 228 can correspond to indentations in one or more of the layers that facilitates separation. Or, the boundary 228 may simply be shown as lines printed on the surface of the material, which provides guidance for where a user should cut to result in an electrode having a desirable size and shape.

The example of FIG. 2C depicts a plurality of polygons, some of which are disposed within one another. This nesting is beneficial for progressively removing pre-determined areas from the example configurable electrode assembly 200, thus reducing an area of the conductive layer 204 to better match an area corresponding to the Broselow scale. For example, for a pediatric patient weighing between 3 and 5 kilograms (kg), the example configurable electrode assembly 200 can be configured by cutting, tearing, or otherwise removing all fields of the electrode except for field 224A, which is color coded grey to correspond to a pediatric patient weighing between 3 and 5 kilograms (kg) on the Broselow scale. In an example configurable electrode assembly 200 in which the electrically conductive layer 204 is coextensive with the example configurable electrode assembly 200 as a whole, removal of all fields 224B-E reduces the size of the electrically conductive layer 204 to a predefined electrode size. In another example, for a pediatric patient weighing between 8 and 9 kg, the example configurable electrode assembly 200 can be configured by cutting, tearing, or otherwise removing all fields of the electrode except for fields 224A, 224B, and 224C, the last of which is color coded red to correspond to a pediatric patient weighing between 8 and 9 kg on the Broselow scale. Even for embodiments in which the conductive layer 204 is not coextensive with the entire area of the example configurable electrode assembly 200, the color coding described above can be a helpful visual cue to confirm an appropriate dose of electrical energy is being provided to a pediatric patient during defibrillation, consistent with the Broselow scale.

FIG. 2C also includes an exploded view of a junction of multiple boundaries that, in one example, can define a hole. The hole at a junction of boundaries can be pre-cut so that corners of the various fields adjacent to the junction of boundaries are rounded after separation one portion from another portion. In such cases, the pattern may define a relatively straight line along which the user is to cut or tear. Yet, by including this "rounding" feature (e.g. predefined hole), a straight cut and/or tear along the boundary may result in a relatively rounded edge. As described herein, having rounded corners for defibrillator pads can be beneficial, for example, so as to provide for more evenly distributed current or energy applied to the patient and avoiding what could lead to high density charge build up than may otherwise be the case. Cutting or tearing along relatively sharp edges on the outer surfaces of the electrode assembly may allow for electrical current or energy to collect in an undesirable manner, which may lead to exposure of the sharp edges to adjacent skin tissue. Such exposure of sharp edges may be a source of harm (e.g., electrical burning) to the patient upon contact with skin tissue.

Figure 2D:
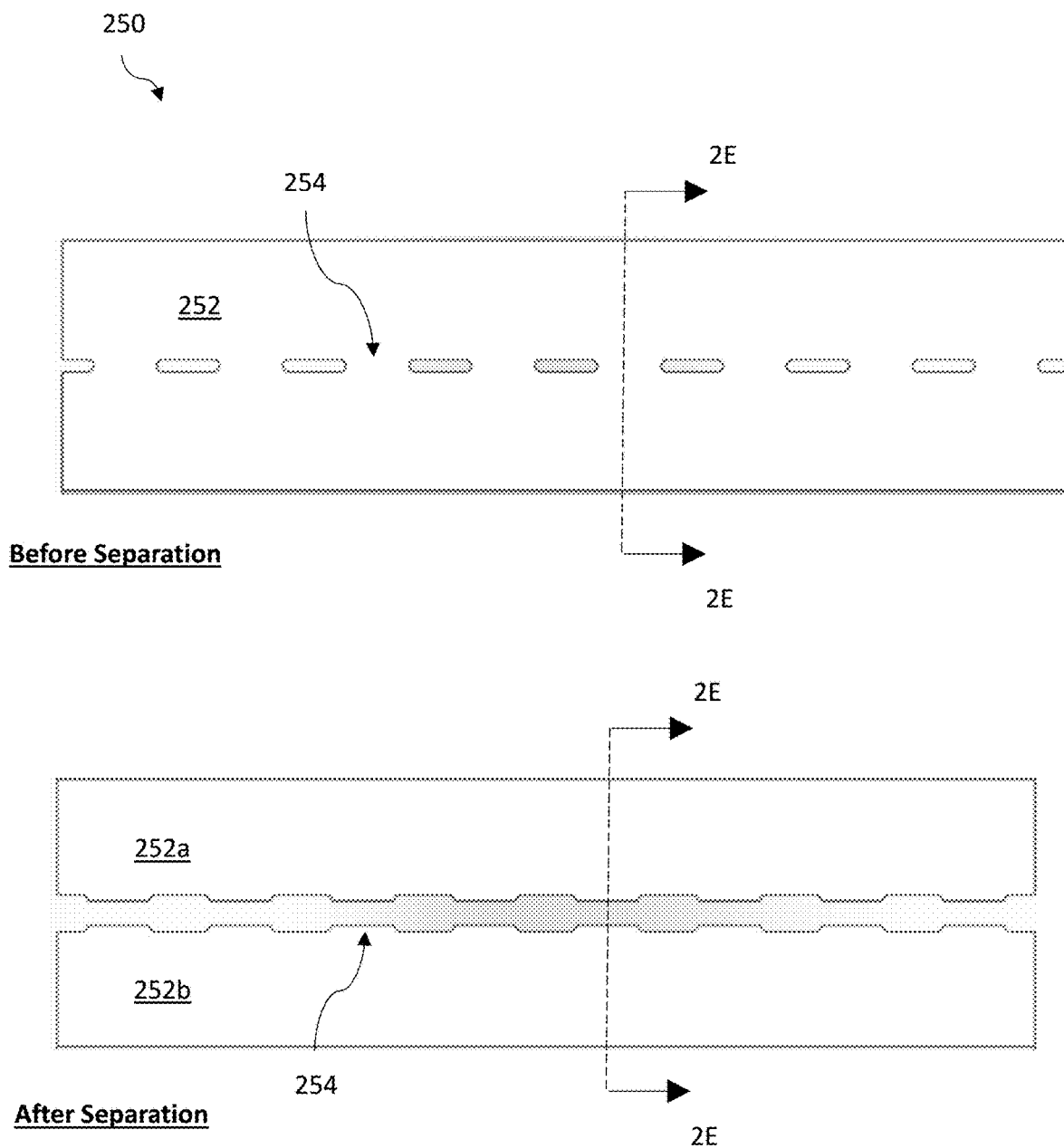
FIG. 2D is a top view of a scored region of a configurable electrode assembly before and after separation, in an example.
Figure 2E:
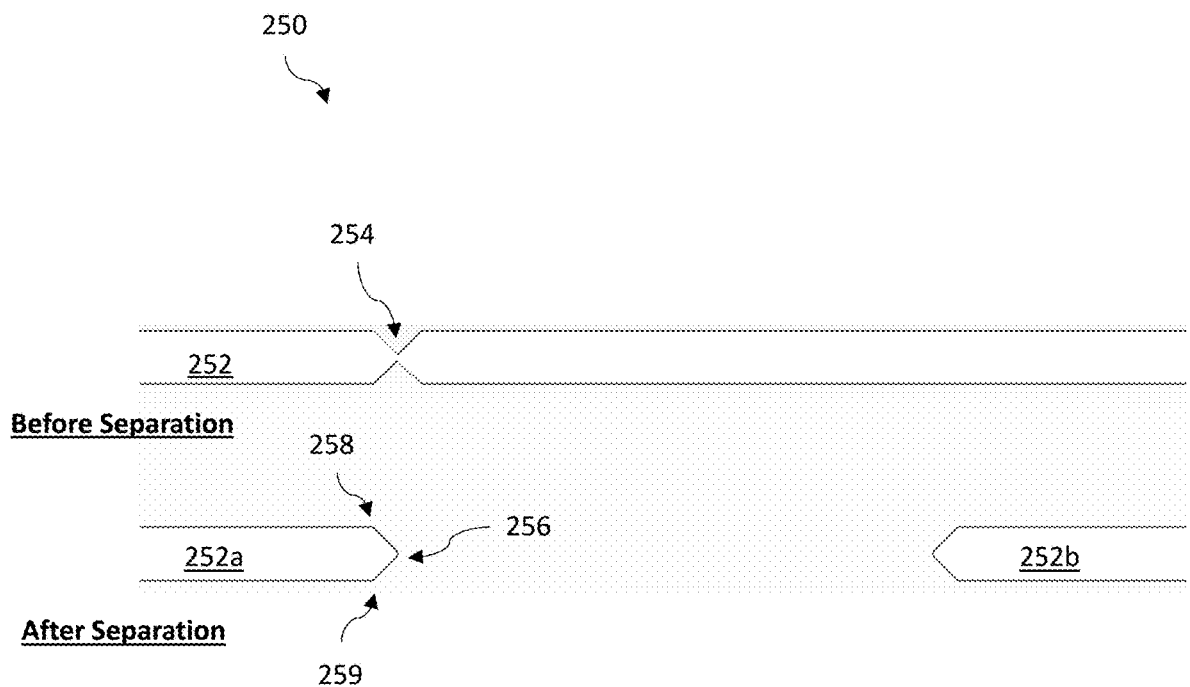
FIG. 2E is a cross-sectional view of the scored region of the configurable electrode assembly of FIG. 2D.

FIGS. 2D and 2E depict various views of a configurable electrode assembly 250 having an electrically conductive layer 252 that includes scored regions 254, which allow for separation of the conductive layer 252 into detached sections 252a, 252b. The scored regions 254 are constructed such that upon separation thereof into sections 252a, 252b, the remaining edges of the sections 252a, 252b that result from the separation (where such edges may be relatively sharp and, as result, prone to high density charge accumulation) are less likely to be undesirably exposed or otherwise oriented toward the outer surface of the electrode. If the separated edges of the sections 252a, 252b are kept away from the outer surface of the electrode, such edges will be less prone to coming into contact with adjacent skin tissue, reducing the overall risk of patient burning or injury.

For instance, as shown in FIG. 2E, the scored region 254 is provided as a V-score cut that yields a relatively clean separation between sections 252a, 252b upon separation thereof. As depicted, upon separation of the conductive layer 252, the sharp edge 256 created from the separation generally remains at a central portion of the separated section 252a, oriented away from the outer surfaces 258, 259 of the section 252a. Such outer surfaces 258, 259 are exposed to the skin of the patient, and so if sharp conductive electrode edges are located at the outer surfaces, then the patient may be at risk of undesirable exposure to high density charge build up. For example, a typical perforation or hole without a cut having a configuration such as the V-score cut, upon separation, may give rise to a relatively sharp edge (e.g., right angle or more acute angle at the point of separation) that is more likely to be exposed and/or in close proximity to the patient's skin upon separation. As discussed above, such an exposed sharp edge may lead to relatively high current or energy densities (e.g., due to defibrillation discharge) in close vicinity to the patient's skin and, hence, may be harmful to the patient.

FIGS. 3A-3C, 4, 5, and 6 depict other examples of electrode assemblies of the present disclosure, each of which is shown to include a different pattern identifying portions of the electrode assembly separable from one another.

Figure 3A:
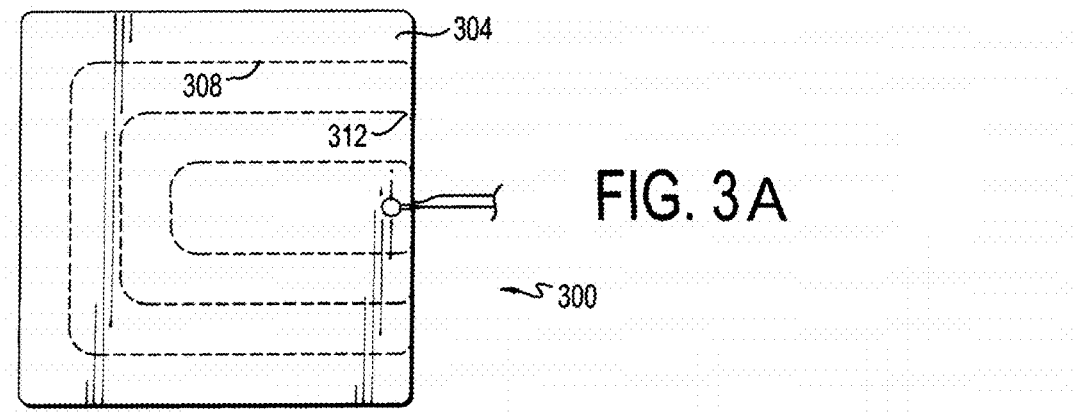
FIG. 3A is a plan view of a configurable electrode assembly that includes a pattern disposed on the electrode assembly for configuring the electrode assembly size, in an example.
Figure 3B:
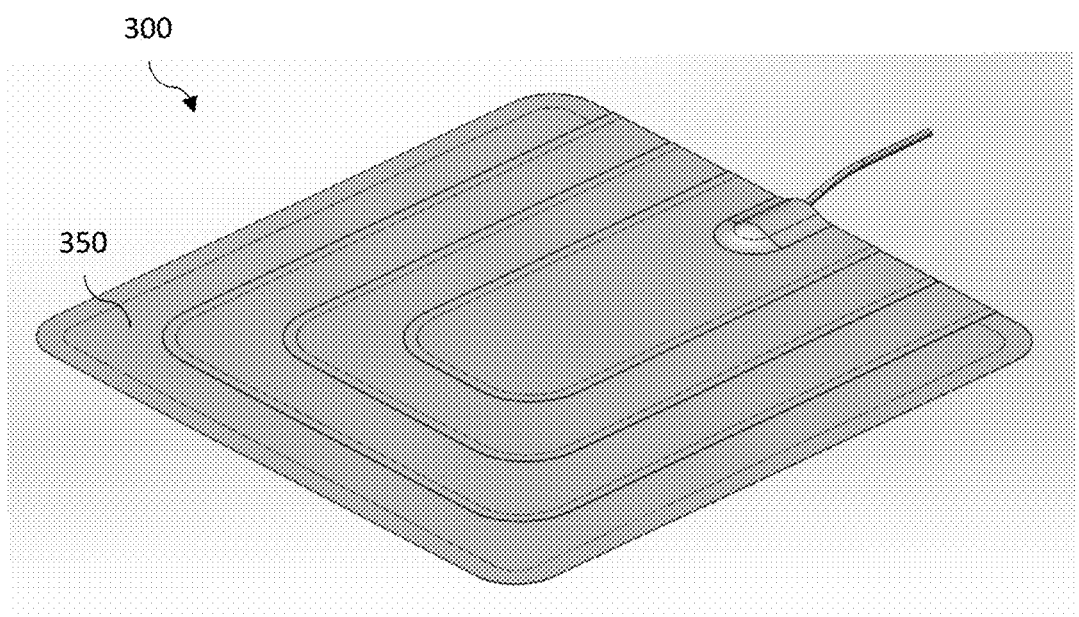
FIG. 3B is a plan view of the configurable electrode assembly of FIG. 3A further including respective backings for separable regions, in an example.
Figure 3C:
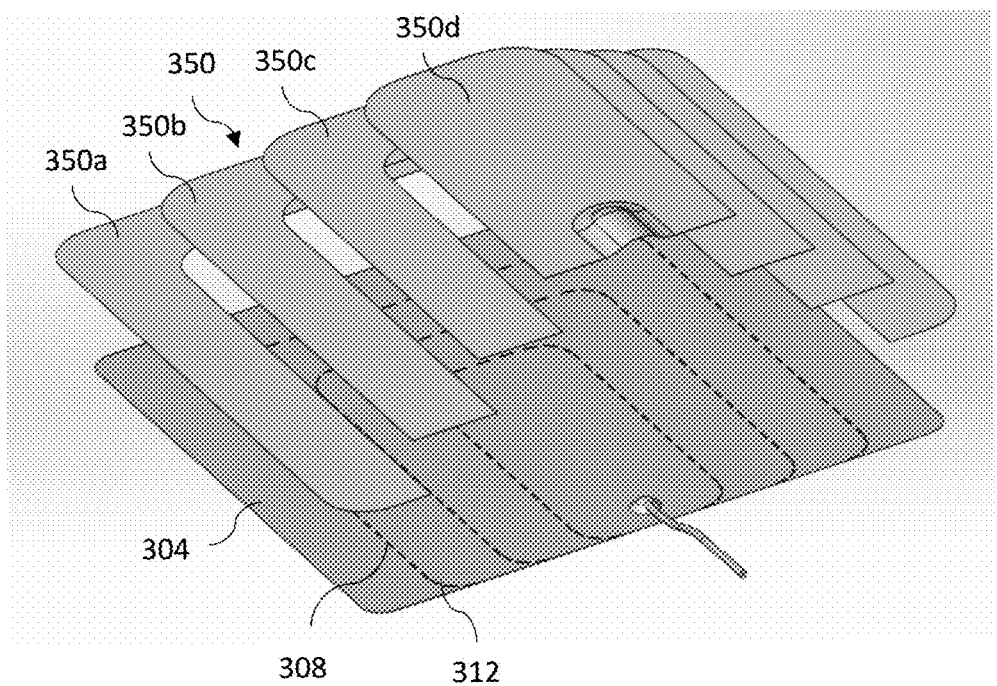
FIG. 3C is an exploded plan view of the configurable electrode assembly of FIG. 3B.

The example configurable electrode assembly 300 shown in FIGS. 3A-3C includes a pattern of polygons (e.g., approximately rectangular in shape) formed as separable regions 304, each of which including a portion having an aspect ratio of greater than 1:1. As also shown, the separable regions 304 are disposed within one another in a nested fashion. While in the example of FIG. 3A, the electrode assembly includes conductive material made up of separable regions 304, FIGS. 3B and 3C further show a support backing 350 provided (e.g., laminated, layered, attached, adhered, in contact with) over the separable regions 304 of the electrode. The support backing 350 may be provided as distinct strips 350a, 350b, 350c, 350d that are overlaid on top of respective separable regions 304. The strips 350a, 350b, 350c, 350d may dimensioned so as to be flush with the boundary 308, or alternatively may slightly overlap the boundary 308, as shown in FIGS. 3B and 3C, so as to ensure full coverage of the support backing 350 over the conductive electrode portion. Constructing the support backing 350 as distinct strips 350a, 350b, 350c, 350d already separated from one another may allow for convenient separation of particular strips of the backing 350 together with the underlying separable regions 304 of the electrode. Hence, particular segments of the electrode assembly 300 (including corresponding conductive electrode and support backing regions) may be easily separated from one another. Or, in other cases, the support backing 350 may be provided as a single piece having perforations, score lines, or the like, which are suitably aligned with the boundary 308, for effective separation of respective segments. It will be understood, particularly in light of FIG. 2B that other polygons, and combinations of nested polygons, can also be depicted as a pattern on a configurable electrode assembly.

Returning to FIGS. 3A-3C, prior to use, one or more of the separable regions 304 may be separated from the other regions of the electrode assembly either by cutting or tearing (e.g., using perforations described above that are optionally includes in some examples) along boundary 308. As also described above, removal of one portion of the example configurable electrode assembly 300 from a second portion can be to adjust the size of an electrically conductive layer (not shown) of the example configurable electrode assembly 300, thus changing the energy density applied to a patient during defibrillation. Also, the generally rectangular in shape separable regions 304 can be separated from one another to adjust the size of the electrode assembly 300 as whole to better fit on a thorax of a patient.

In the example configurable electrode assembly 300 shown, the boundaries 308 each define a curved edge 312 at corners of each perimeter edge of the separable regions 304. The curved edge 312 helps prevent high energy densities that can collect at sharp corners (e.g., corners having an acute angle or right angle) during defibrillation. This, in turn, can help reduce burning of the patient resulting from defibrillation. The curved edge 312 at the corners of the example configurable electrode assembly 300 is shown in other examples herein and is optionally applicable to even the examples in which the curved edge 312 is not shown.

Figure 4:
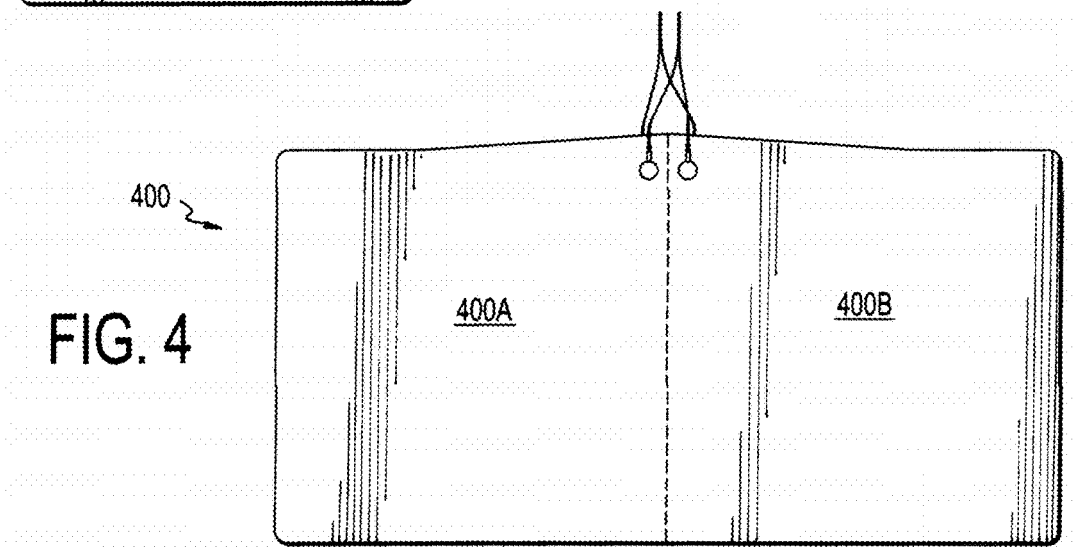
FIG. 4 is a plan view of a configurable electrode assembly with a pattern providing guidance for separating the electrode assembly, in an example.

FIG. 4 illustrates an example configurable electrode assembly 400 in which the pattern is simply a straight line dividing the electrode assembly 400 into a first portion 400A and a second portion 400B, which may be conveniently separated from one another using any of the methods (e.g., cutting, tearing at a perforation, tearing at an indented and/or thinned region) described above. The first portion 400A and the second portion 400B are connected to corresponding lead wires and terminals, that in turn connect each of the first portion 400A and the second portion 400B to a power source. The example configurable electrode assembly 400 provides added convenience because a health care practitioner may simply handle the example configurable electrode assembly 400 as a single unit, rather than two independent units, until the portions 400A and 400B are separated from one another and each portion placed on a patient prior to defibrillation.

Figure 5:
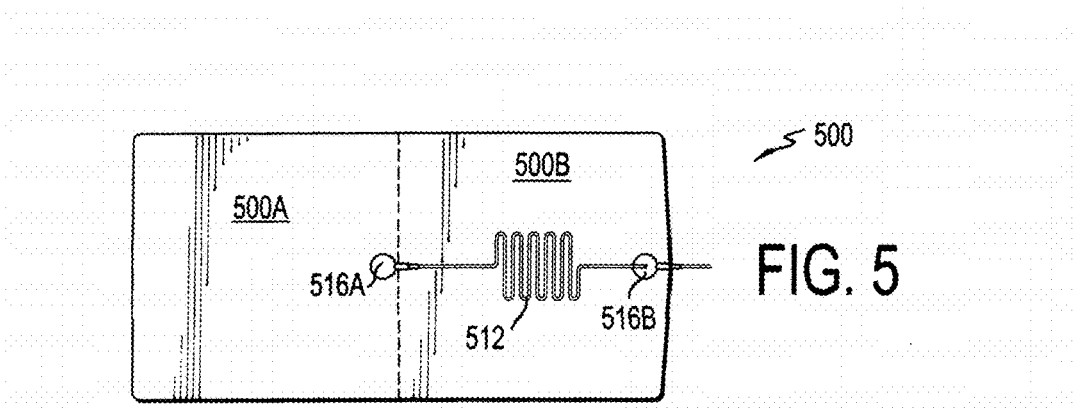
FIG. 5 is a plan view of a configurable electrode assembly that includes a first portion separable from a second portion, in which the first portion and the second portion are connected to each other by a conductor after being separated, in an example.

FIG. 5 illustrates an example configurable electrode assembly 500 similar to the example configurable electrode assembly 400. As with the example configurable electrode assembly 400, the pattern of the example configurable electrode assembly 500 is simply a straight line dividing the electrode assembly 500 into a first portion 500A and a second portion 500B. These portions may be conveniently separated from one another using any of the methods (e.g., cutting, tearing at a perforation, tearing at an indented and/or thinned region) described above. In addition, the first portion 500A and the second portion 500B of the example configurable electrode assembly 500 are electrically connected to each other using at terminals 516A and 516B via a conductor 512. The connection of the first portion 500A and the second portion 500B via the conductor 512 has at least two performance features.

Figure 6:
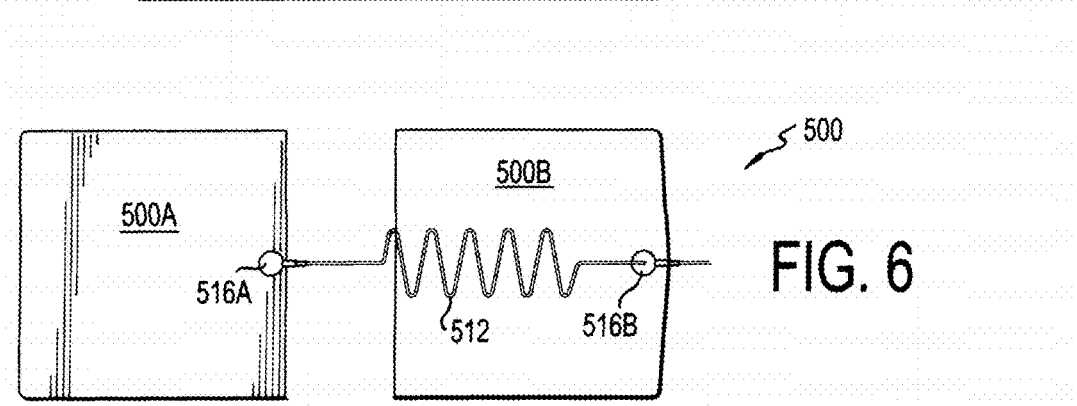
FIG. 6 is a plan view of a configurable electrode assembly that includes a first portion separable from a second portion, in which the first portion and the second portion are connected to each other by a conductor after being separated, in an example.

As shown in FIG. 6, the first performance feature is that only a single lead wire is needed to connect both the first portion 500A and the second portion 500B to a defibrillator power source and/or controller. As also shown in FIG. 6, the second performance feature is that a distance separating the first portion 500A from the second portion 500B can be limited by the length of the conductor 512. Limiting the distance separating the first portion 500A from the second portion 500B maintains an energy density helpful for stimulating the heart of the patient by limiting the area over which electrical energy can diffuse. In contrast, if electrodes of a conventional defibrillator are placed too far apart, the energy density reaching the heart of a patient can be too diffuse to be effective. In examples, the length of the conductor 512 can be from 2 centimeters to 3 centimeters (cm), 2 cm to 5 cm, 2 cm to 10 cm, 3 cm to 5 cm, 3 cm to 8 cm, 3 cm to 10 cm, 5 cm to 10 cm, 8 cm to 12 cm, and in some examples approximately 10 cm long. In some embodiments, it may be preferable for the electrical energy to be distributed across a greater area, or to be generated from multiple locations. Hence, when the electrode assembly 500 is separated, the electrical current may originate from the separate locations provided by the first portion 500A and the second portion 500B. The electrical current may then travel through the heart according to one or more vectors more desirable for defibrillation as compared to if the electrical current originated from the more compact electrode assembly prior to separation.

High Aspect Ratio Electrode Assemblies

The example patterns described above for depicting at least one boundary at which a first portion of an electrode assembly is separable from a second portion are applicable in other contexts. For example, applications described below in the context of FIGS. 7 to 9 include patterns that depict at least one boundary at which a first portion of an electrode assembly is separable from a second portion so that at least two high aspect ratio electrodes may be used to apply electrical energy to a patient during defibrillation. The pattern and boundaries described above are equally applicable to examples having high aspect ratios, as described below in more detail.

Figure 7A:
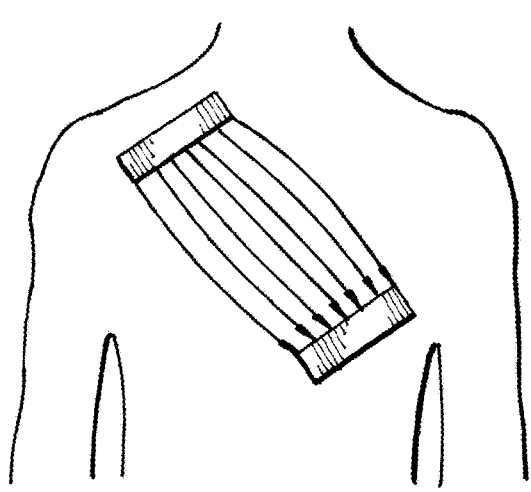
FIG. 7A is a schematic illustration of electrical field flux lines between two high aspect ratio electrodes, in an example.
Figure 7B:
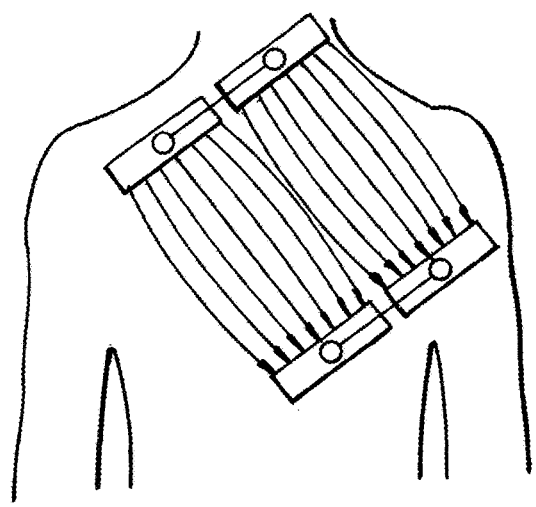
FIG. 7B is a schematic illustration of electrical field flux lines between two sets of electrodes in which the electrodes in each set are separated from one another yet remain electrically connected to distribute electrical energy over a larger area, in an example.

As schematically shown in FIG. 7A, high aspect ratio electrode assemblies oriented on a patient to be parallel to one another may produce more uniform fields of electrical energy between the electrode assemblies upon defibrillation, which can improve the effectiveness of the defibrillation. As schematically shown in FIG. 7B, high aspect ratio electrode assemblies, such as those in which multiple electrode assemblies are electrically connected (as shown in FIG. 9B for example) may also be used to increase and/or adjust the area over which electrical energy is distributed during defibrillation without requiring additional contact area on the patient. For example, it may be preferable for the defibrillation current to reach a wider area than otherwise would be the case if the electrode assembly were not separable. Or, the vector(s) along which the defibrillation current travels may also be adjusted according to how the electrodes are separated and subsequently placed.

Figure 8:
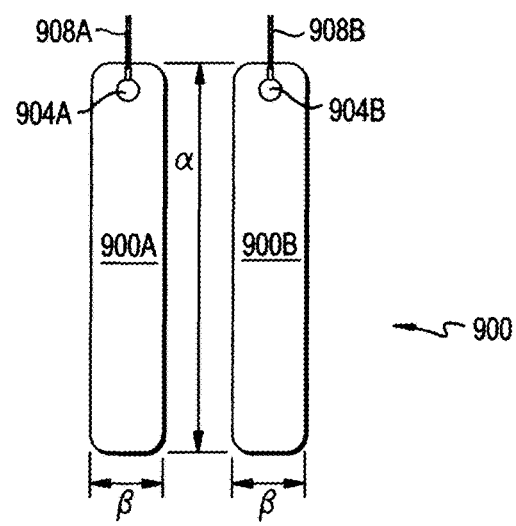
FIG. 8 is a plan view of high aspect ratio electrodes, in an example.

An example high aspect ratio electrode assembly 900 is shown in FIG. 8 and optionally includes two portions separable from one another: 900A and 900B. Each of these includes a corresponding terminal 904A and 904B that connects each portion 900A and 900B to a lead wire 908A and 908B, respectively.

Each of the high aspect ratio electrode assembly portions 900A and 900B is shown as having a first dimension of a and a second dimension $\beta$. The aspect ratio of $\alpha:\beta$ is, in some examples greater than 1:1. In other examples, the aspect ratio is greater than any one or more of 2:1, 3:1, 4:1, 5:1, 6:1, 7:1, 8:1, 9:1, 10:1, 11:1, 12:1, 13:1, 14:1, 15:1, or greater, for example, up to 20:1, 30:1, etc.

Figure 9A:
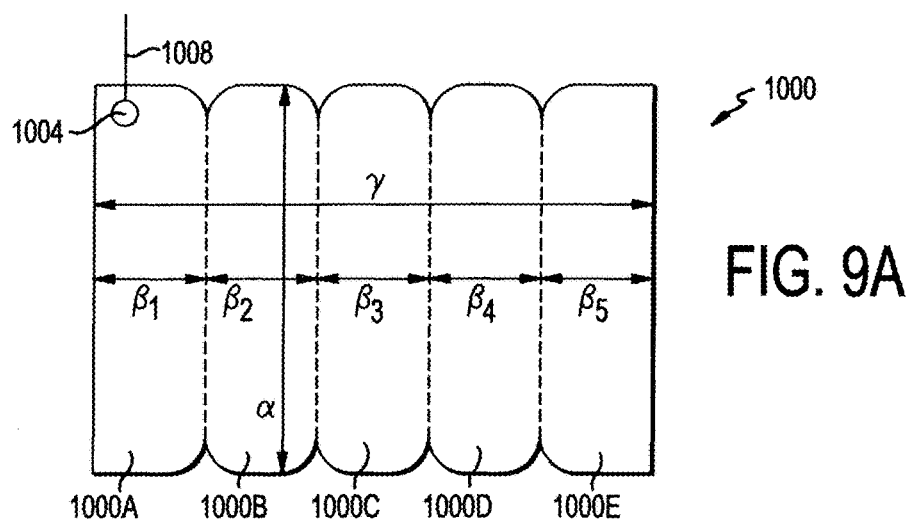
FIG. 9A is a plan view of an electrode assembly comprising a plurality of high aspect ratio electrode assemblies separable from one another according to a pattern disposed on the electrode assembly, in an example.
Figure 9B:
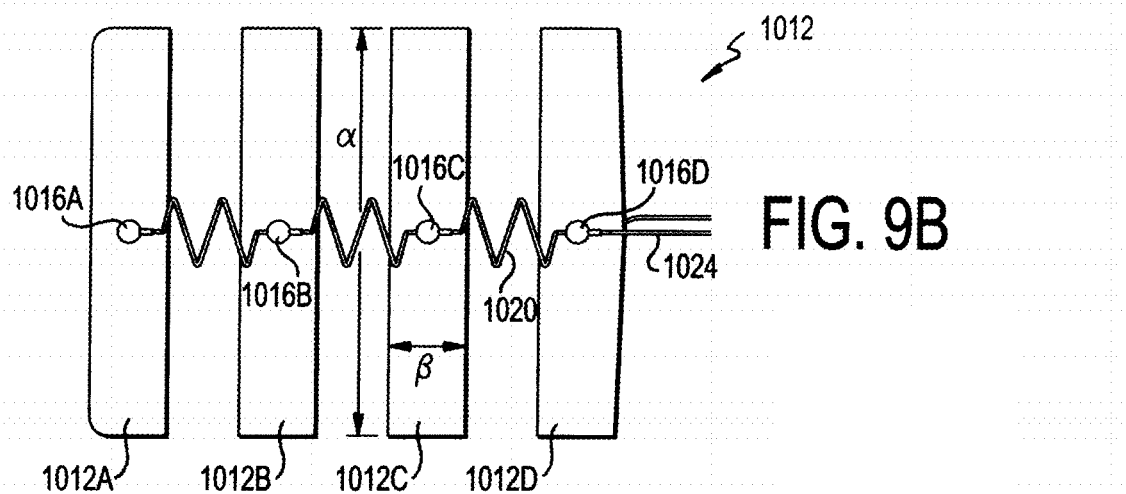
FIG. 9B is a plan view of an electrode assembly comprising a plurality of high aspect ratio electrode sub-assemblies separable from one another using a pattern disposed on the electrode assembly and in which each of the plurality of high aspect ratio electrode assemblies are connected to one another with an electrical conductor after being separated, in an example.

As shown in FIG. 9A, an example configurable electrode assembly 1000 includes individual portions 1000A-E that may be initially joined together and may depict a pattern that provides guidance regarding the separation of the portions. In this example, the pattern providing guidance regarding separation of the portions is a pattern of parallel lines that, in this example, show each portion as having an approximately rectangular shape having any of the aspect ratios described above in the context of FIG. 8, as understood by those of ordinary skill in the art. Such an approximately rectangular shape may include a shape having right angles, beveled edges, rounded corners, or other appreciable variations thereof. In the example shown in FIG. 9A, terminal 1004 is attached to portion 1000A and to lead wire 1008. For this reason, portions may be progressively removed starting with 1000E up to 1000B, thus increasing the aspect ratio progressively from $\alpha:\beta$ to $5\alpha:\beta$, in which $\alpha:\beta$ is greater than any one or more of 2:1, 3:1, 4:1, 5:1, 10:1, etc. Also, some examples of the configurable electrode assembly 1000 includes a conductive layer coextensive with the entire area of the electrode assembly 1000 (except for an optional a non-conductive border around the perimeter) so that the area of the conductive layer is reduced upon successive removal of individual sections 1000E to 1000B. Furthermore, much like the example shown in FIGS. 3A-3C, each of the portions 1000A-E includes a curved edge at corners rather than acute angular or right angular corners.

FIG. 9B shows a variation of example configurable electrode assembly 1000. In the example configurable electrode assembly 1012 shown, the individual portions 1012A-D are connected by a conductor 1024. The conductor 1024 is attached to each individual portion 1012A-D at a corresponding terminal 1016A-D. Some of the benefits of this configuration are presented above.

Chest Compression Sensor Assembly and Sterile Pouch

Figure 10A:
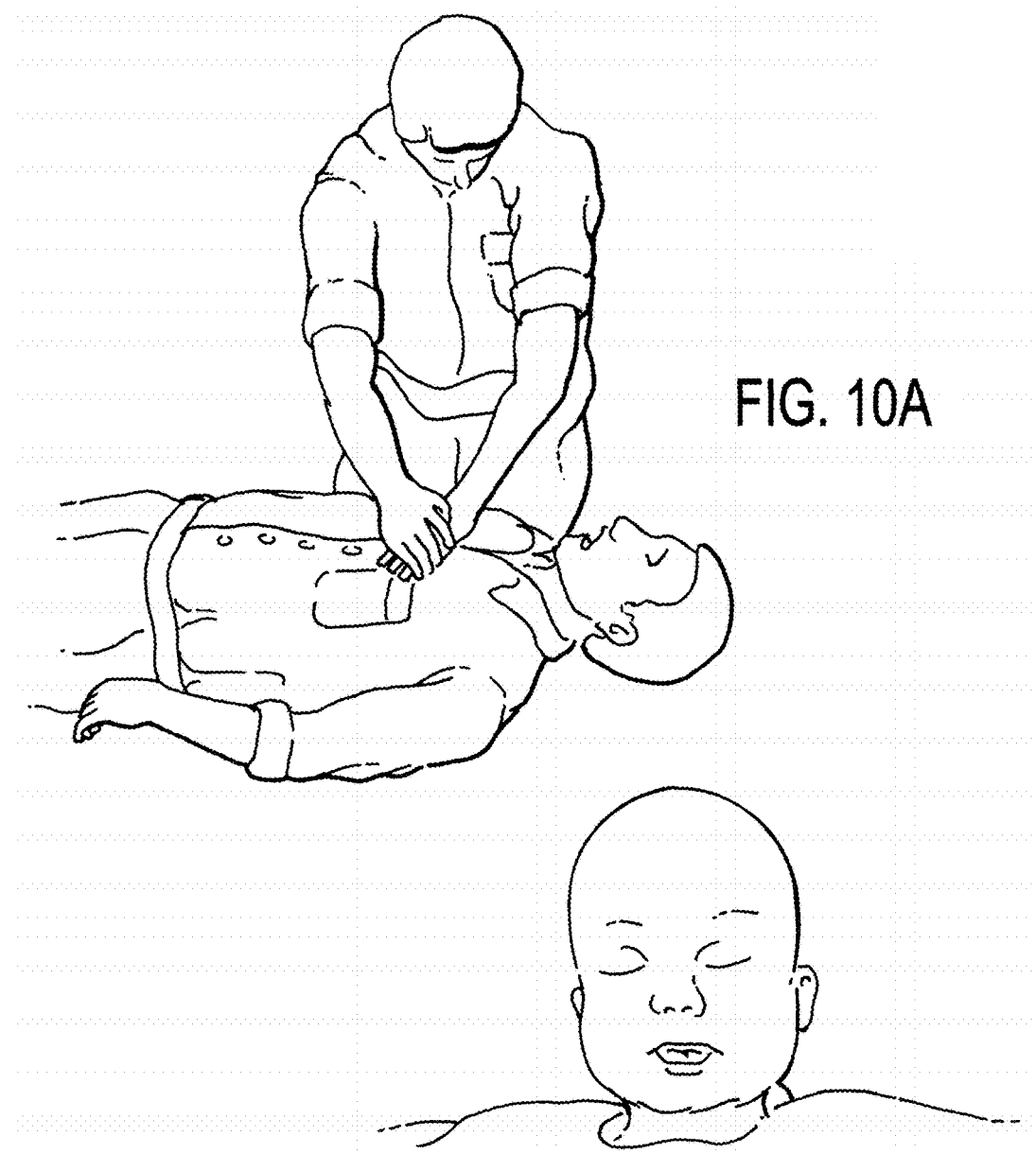
FIG. 10A illustrates a technique for the administration of chest compressions on an adult.
Figure 10B:
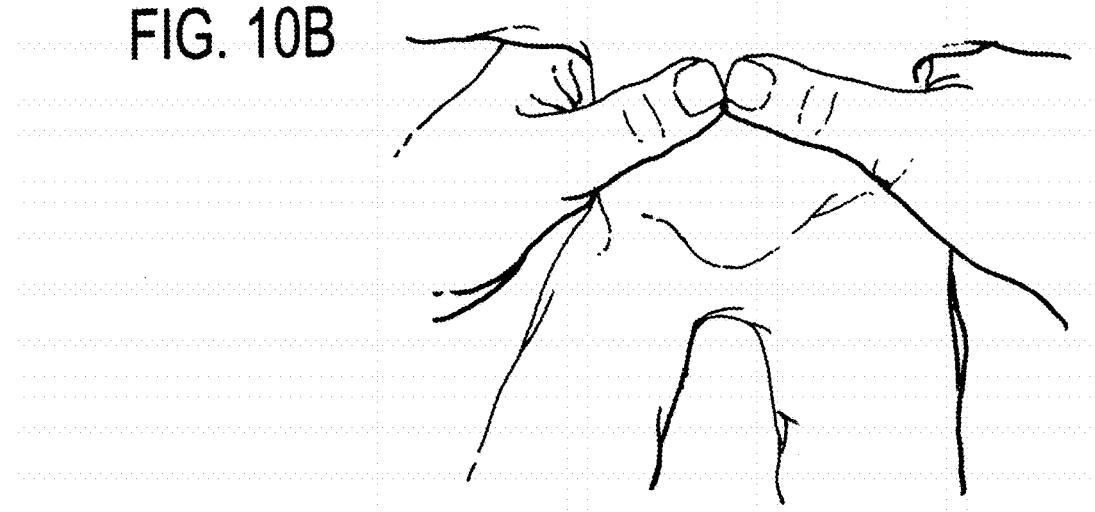
FIG. 10B illustrates a technique for the administration of chest compressions on an infant.

To set the context for some examples of a chest compression sensor of the present disclosure, FIGS. 10A and 10B schematically illustrate applying chest compressions to an adult and an infant, respectively. This context will facilitate explanation of various benefits of examples presented herein.

FIG. 10A illustrates the application of chest compressions to an adult. As shown, the patient is placed on his back. The person administering chest compressions places both hands on the thorax of the patient approximately over the heart of the patient. This enables the weight of the person administering chest compressions to contribute to the force with which the compressions are applied to the patient.

FIG. 10B illustrates the application of chest compressions to an infant. The skeleton and musculature of an infant are more delicate than those of an adult. As such, chest compressions are applied to an infant by gripping the infant as shown in FIG. 10B. The thumbs of the person applying chest compressions are placed on the thorax of the infant. The fingers of the person applying chest compressions are placed on the back of the infant. Chest compressions are then administered by squeezing the thorax of the infant between the thumbs and fingers.

Regardless of whether chest compressions are applied to an adult or an infant, with or without an incision of any type in the thorax, a chest compression sensor can be helpful in improving the effectiveness of chest compressions. A chest compression sensor monitors the rate at which compressions are applied and the depth at which the compressions squeeze the body. These data can then be used to provide instructions to the person administering chest compressions so that the chest compressions are more likely to stimulate the flow of blood in the patient or less likely to injure the patient.

Figure 11A:
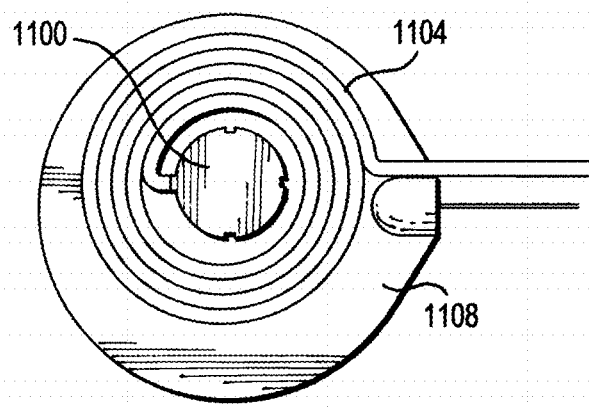
FIG. 11A is a plan view of a removable chest compression sensor substrate, in an example.

FIG. 11A illustrates a chest compression sensor 1100, with an attached lead wire 1104. The chest compression sensor 1100 may be removably coupled to a substrate, for example via an adhesive or a suitable amount of thinned material similar to insulation around wires of a ribbon cable that are easily torn or otherwise separable from one another. The substrate can be an electrode assembly 1108, such as one of the electrode assemblies described above, a polymer sheet, or other type of convenient substrate used for the manipulation of the sensor 1100. This optional coupling of a chest compression sensor 1100 to an electrode assembly 1108 or other substrate may improve the convenience of treatment for patients that require both chest compressions and defibrillation because both of these instruments are initially available as a single unit. In some embodiments, the chest compression sensor 1100 can be in a standby state in which data is either not collected or not analyzed by a connected controller until moved to a patient thorax for use. The chest compression sensor 1100 (or its controller) can detect its placement on a patient thorax and/or being entered into use and being collecting and/or analyzing chest compression data. In some examples, the chest compression sensor 1100 is held in place on the thorax via a low peel strength adhering material, as variously described herein.

The lead wire 1104 in the example shown is coiled so as to avoid tangling and improve the convenience of handling. In some examples, the coiled lead wire 1104 is temporarily held in place by a releasable connection (e.g., via an adhesive) to a surface of the electrode assembly 1108 or other substrate. In other examples, the coiled lead wire 1104 retains the coil conformation until unwound (partially or entirely) because the insulation surrounding the conductive portion of the lead wire 1104 is attached to adjacent windings in the coil. For instance, the insulation may be thin enough so as to be easily torn or allowing for separation of adjacent windings, enabling the lead wire 1104 to be unwound. A user can separate the lead wire 1104 progressively from the attachments to the adjacent coils, thus maintaining the coil for any portion of the length of the lead wire 1104 not needed to be uncoiled.

The chest compression sensor 1100 includes one or more inertial measurement sensors (e.g., accelerometers, gyroscopes, magnetometers) used to monitor various characteristics of chest compressions and used to improve the quality of the chest compressions. In one example, the chest compression sensor 1100 includes at least an accelerometer used to monitor the rate and depth at which chest compressions are applied to a patient receiving chest compressions. In other examples, the chest compression sensor includes other inertial measurement units (e.g., gyroscopes, magnetometers) that can identify other characteristics of the chest compressions, such as force and orientation of the sensor. The data corresponding to these characteristics are transmitted as signals from the chest compression sensor 1100 through a lead wire or wireless transmitter to a controller (not shown) than can interpret the signals, display the characteristics, and provide instructions to improve the delivery of chest compressions.

Figure 11D:
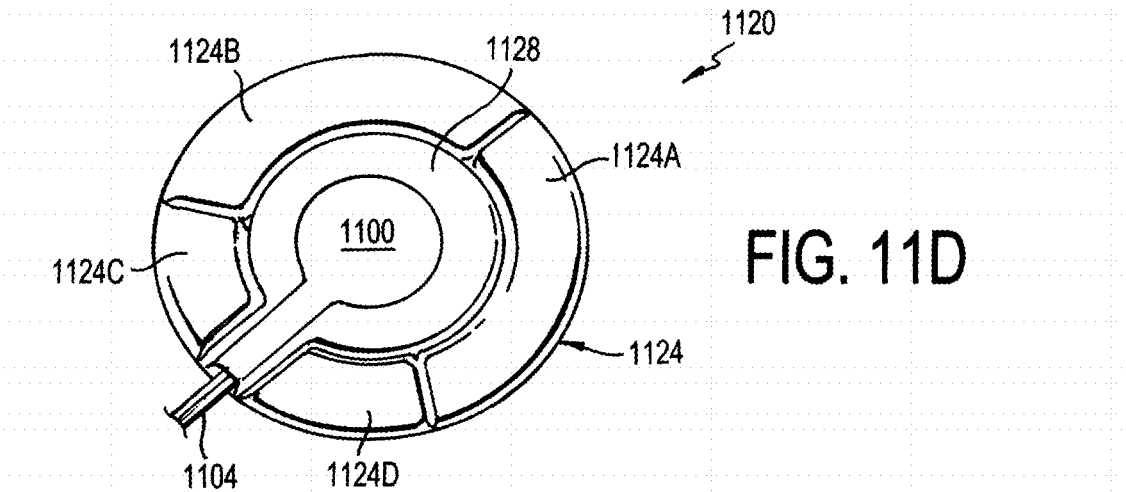
FIG. 11D is a plan view of a chest compression sensor of FIG. 11A encapsulated in a configurable pad, in an example.
Figure 11B:
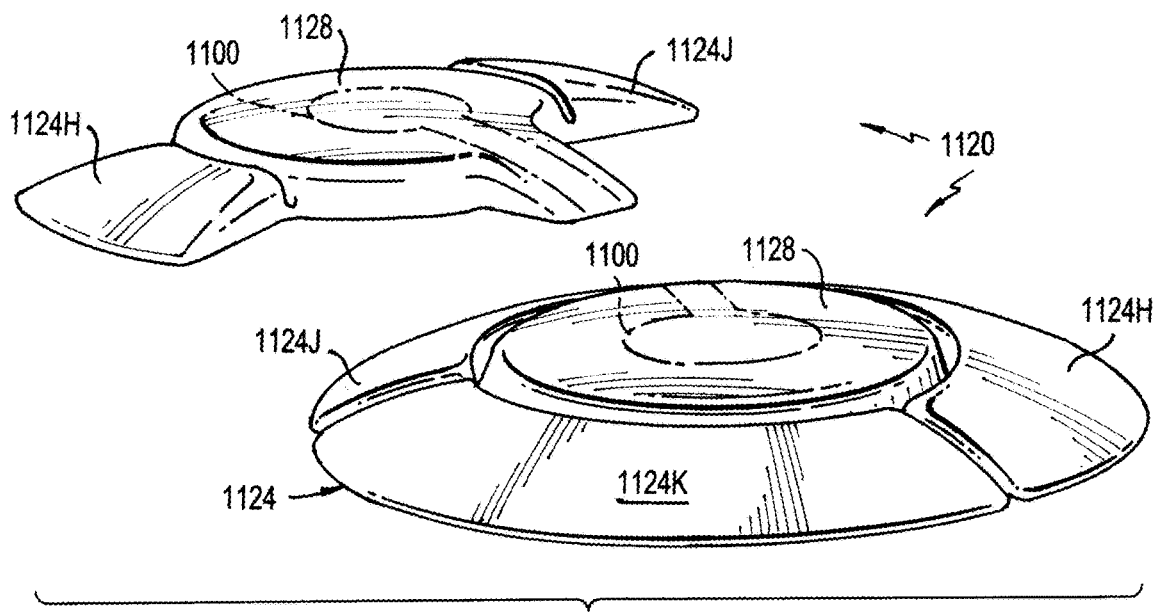
FIG. 11B is a perspective view of a chest compression sensor encapsulated in a configurable pad, in an example.
Figure 11C:
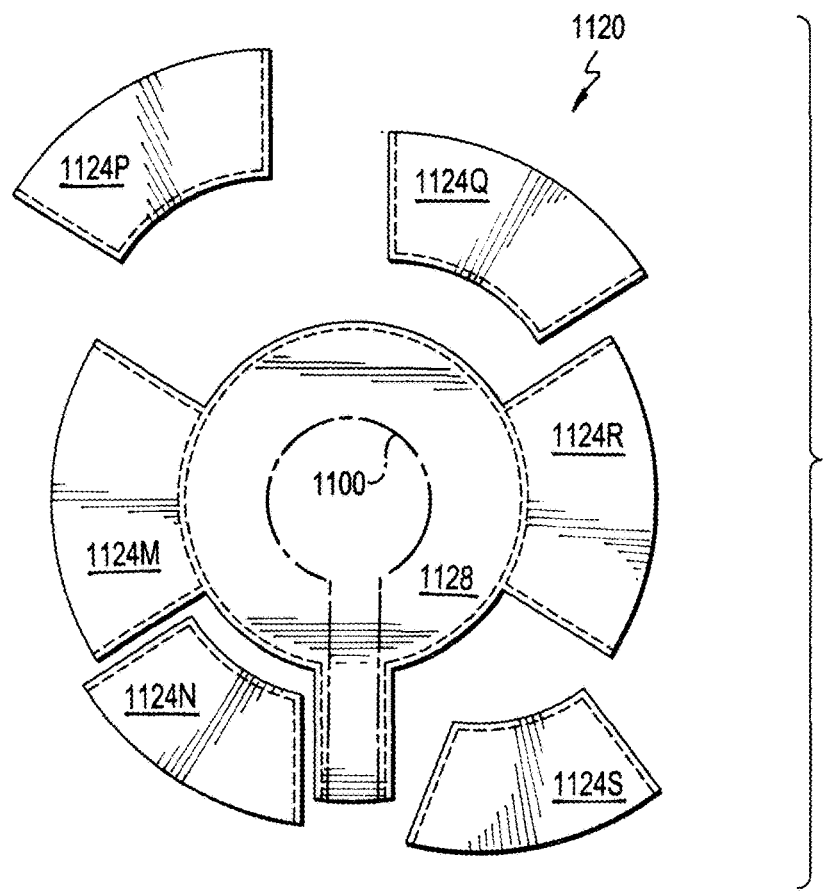
FIG. 11C is a plan view of a configurable pad encapsulating a chest compression sensor with several tabs removed, in an example.

FIGS. 11B and 11C show examples of the chest compression sensor assembly 1120 that includes a chest compression sensor 1100 that has been encapsulated in a polymeric (or other covering material) placement pad 1124. In examples, the surrounding encapsulation provides comfort for the hands (and/or thumbs) of the person applying chest compressions. In some cases, the covering material may protect the hands and/or thumbs from injury from sternal wires that may be present in the patient after a sternotomy or other surgery using wires. The covering material may also provide a source of traction for the provider of chest compressions, which can slip on bare skin that is covered by blood, sweat, or other lubricating material. Any suitable covering material may be used. For example, the covering material may include a silicone, elastomer, rubber, polymeric material, polyurethane, gel, or any other appropriate material for housing the chest compression sensor. In some embodiments, the covering material may be used as an adhering material. As shown in FIGS. 11B and 11C, the covering material may completely encapsulate the chest compression sensor 1100. However, the covering material need not encapsulate the entirety of the chest compression sensor and, in some cases, may only partially cover the sensor. For example, the covering material may provide comfort and/or protection at certain parts of the chest compression sensor (e.g., directly on top), yet may allow other parts of the sensor to be exposed.

Analogous to examples described above, the placement pad 1124 includes a pattern of boundaries (e.g., molded features, printed lines) configured for removing some or all of the placement pad 1124 (analogous to the pattern described above in the context of the configurable electrode assembly) so that the shape of the placement pad 1124 can be configured to suit the available space on a patient thorax or a particular application. Other examples of chest compression sensor assemblies 1120 may include other boundaries, such as those described above, that use perforations, an image layer, a protective mask, or combinations thereof.

As shown in FIG. 11B, the placement pad 1124 includes a center portion 1128 in which the chest compression sensor 1100 is encapsulated. Perimeter portions 1124H, 1124J, and 1124K of the placement pad can be selectively removed. In one view of an example shown, perimeter portion 1124K has been removed, leaving perimeter portions 1124H and 1124J. This particular configuration can be helpful for the administration of chest compressions to an infant because the thumbs of the person applying the chest compressions can be placed on perimeter portions 1124H and 1124J.

FIG. 11C shows another example of a chest compression sensor 1100 that has been encapsulated in a polymeric placement pad 1124. In this example, the chest compression sensor 1100 is disposed within the center portion 1128. Perimeter portions 1124M, 1124N, 1124P, 1124Q-S are defined by a pattern that can be used to remove one or more of the portions so that the polymer placement pad 1124 can be configured. As shown, similar to that shown in FIG. 11B, the perimeter portions 1124P, 1124Q, 1124N, 1124S have been removed, leaving perimeter portions 1124M and 1124R, which provides comfort for the thumbs of a person while administering chest compressions in an infant CPR configuration.

FIG. 11D is a plan view of another example compression sensor 1100 (connected to a controller via lead wire 1104) that has been encapsulated in a polymeric placement pad 1124. In this example, the chest compression sensor 1100 is disposed within the center portion 1128. Perimeter portions 1124A, 1124B, 1124C, and 1124D are defined by a pattern that can be used to remove one or more of the portions so that the polymer placement pad 1124 can be configured.

The placement pad 1124 also includes a side for adhering the chest compression sensor to a patient, analogous to the adhering material described above in the context of FIGS. 2A, 2B, and 2C. That is, the adhering material may serve to mechanically couple the chest compression sensor to the patient, yet exhibit a low peel strength material so that it can be removed from the patient with a reduced force so that an incision is less likely to be unintentionally re-opened upon removal of the placement pad 1124. In examples, the adhering material may extend over some or all of the placement pad 1124. For example, the adhering material side may only be on a side of center portion 1128 opposite to the face shown in any of FIGS. 11B and 11C. Or, in some cases, the covering material itself may function as an adhering material. For example, the covering material may be made up of a polymer (e.g., polyurethane, elastomer, silicone, polyester, plastic, rubber, amongst others) that acts as a relatively weak adhesive.

In the case of a patient with a thoracic incision (including, but not limited to those illustrated above in FIGS. 1A-1F), placement of the chest compression sensor at a location on a thorax proximate to a patient's heart but within a sterile field surrounding an incision can increase the risk of infection.

Figure 12:
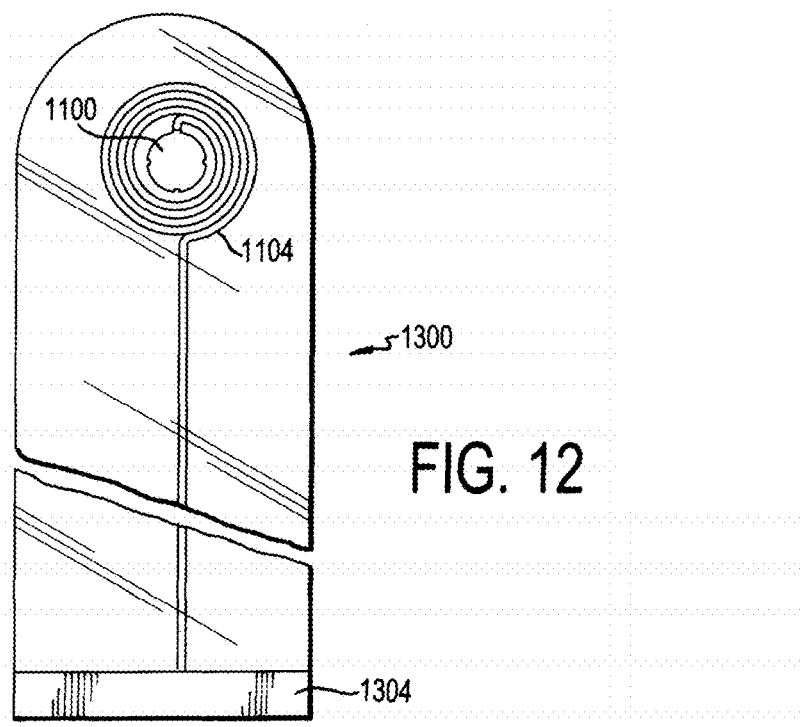
FIG. 12 is a schematic illustration of a chest compression sensor encased in a sterile pouch, in an example.

To address this problem, FIG. 12 depicts a sterile pouch 1300 configured to hold a chest compression sensor 1100 (or a chest compression sensor assembly 1120). As shown, the chest compression sensor 1100 may be placed within the sterile pouch 1300 prior to placement of the sensor at the location on the patient's thorax, and thus stored within a sterile space prior to use. In the example shown in FIG. 12, the chest compression sensor 1100 and lead wire 1104 are stored in the sterile pouch, which is provided with the defibrillation electrode. In other examples, the chest compression sensor 1100 may be releasably attached to a defibrillation electrode assembly, both of which can be stored within the sterile pouch 1300. That is, it is possible for the defibrillation electrode itself to be provided in a sterile package or container. Regardless, prior to use, one or both of the chest compression sensor 1100 and/or the defibrillation electrode assembly are removed from the sterile pouch and placed on a patient. Because one or both of the chest compression sensor 1100 and the defibrillation electrode assembly were sterile and stored in the sterile pouch 1300, one or both may be placed within a sterile field surrounding an incision and used to monitor chest compressions performed on the patient and defibrillate the patient, respectively. In this way, the chest compression sensor can still be used to monitor the characteristics of the chest compressions and not introduce contaminants or pathogens into the sterile field. The sterile pouch 1300 is also configured to hold at least a portion of a lead wire 1104 attached to the sensor 1100 so both the sensor and the lead wire can be placed in the sterile field without introducing contaminants or pathogens into the sterile field. A sealed closure, such as a peelable strip 1304 seals the sterile pouch 1300 from contamination after the chest compression sensor 1100 has been sterilized and before it has been removed from the sterile pouch 1300 for placement on a patient. That is, the sealed closure may be able to maintain the chest compression sensor within the sterile space, and opening of the sealed closure exposes the chest compression sensor to the surrounding environment, allowing for removal and placement of the sensor. It can be appreciated that sealed closures other than a peelable strip may be employed, such as a zipper closure, tearable seal, amongst others.

Figure 13:
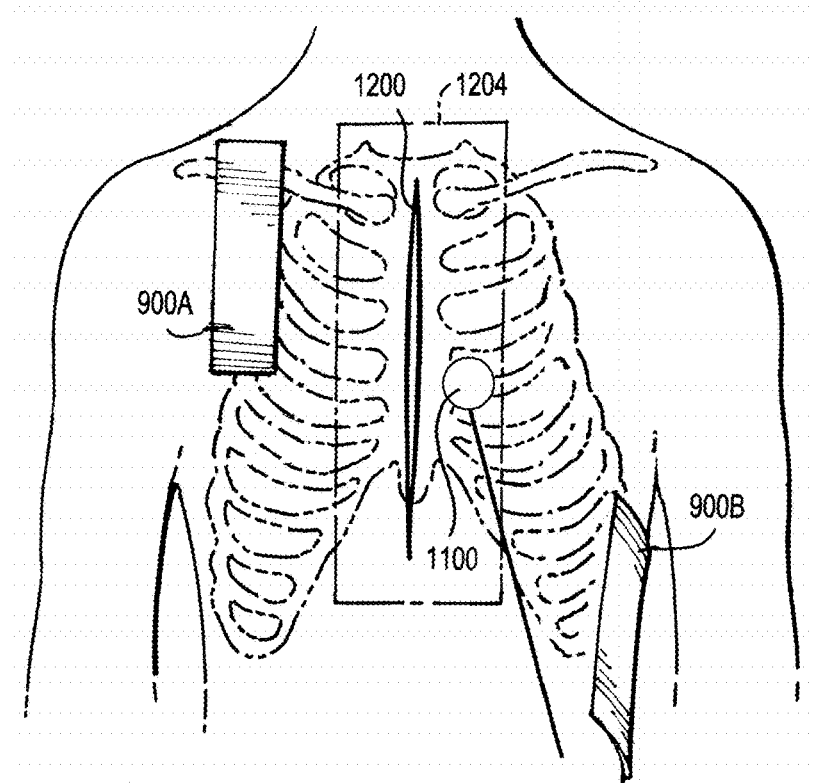
FIG. 13 is a plan view of a chest compression sensor previously stored in a sterile pouch and subsequently placed within a sterile field of a transthoracic incision, in an example.

FIG. 13 illustrates placement of a chest compression sensor 1100 within a sterile field 1204 around a transthoracic incision 1200 after the chest compression sensor 1100 has been removed from the sterile pouch 1300. For illustration, configurable defibrillation pads 900A and 900B are also shown on the thorax. In some examples (not shown in this figure), the chest compression sensor is placed directly over the sternum during chest compressions. In the case of FIG. 13, the chest compression sensor would be placed on the transthoracic incision. Accordingly, as noted above, for chest compression sensors that are mechanically coupled to the patient, it may be beneficial for the portion of the chest compression sensor that contacts the sensitive region to exhibit a relatively low peel strength, to avoid injury to the patient due to chest compressions. Alternatively, for some embodiments, the chest compression sensor does not mechanically couple to the patient at all, and so does not exhibit any appreciable peel strength.

CPR Compression Assembly

Figure 14:
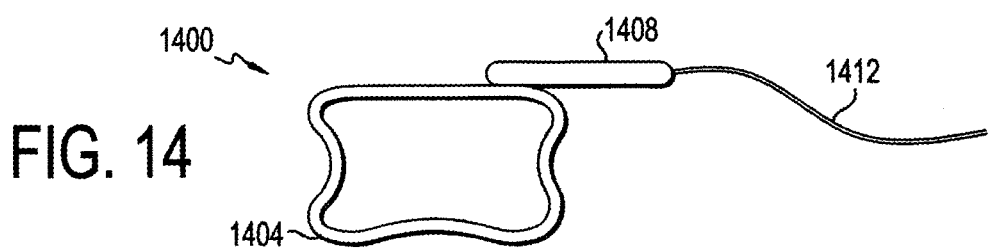
FIG. 14 is an illustration of a chest compression sensor attached to a wristband, in an example.
Figure 15A:
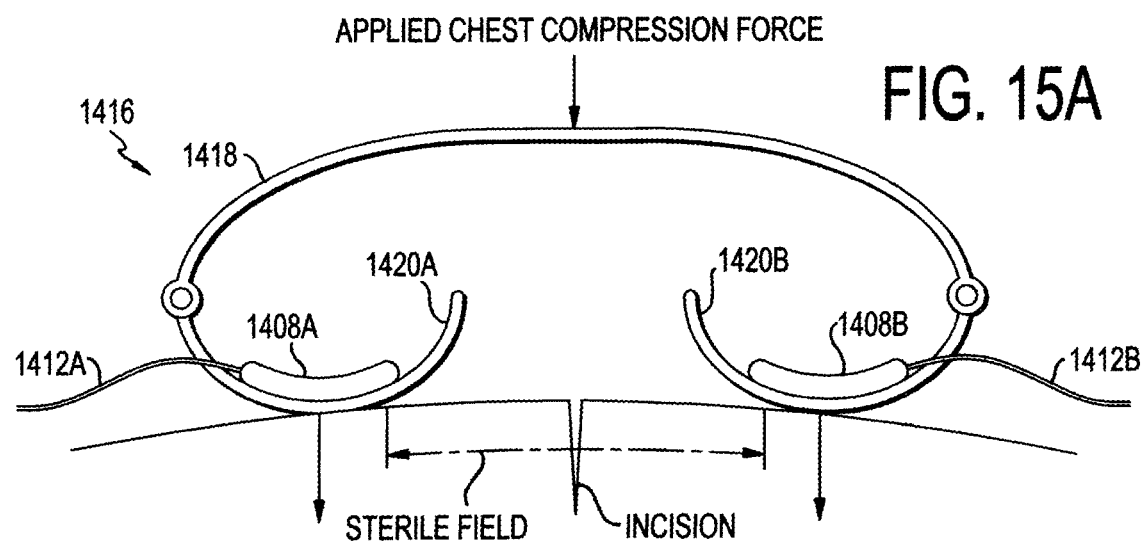
FIG. 15A is a side view of a chest compression assembly, in an example.
Figure 15B:
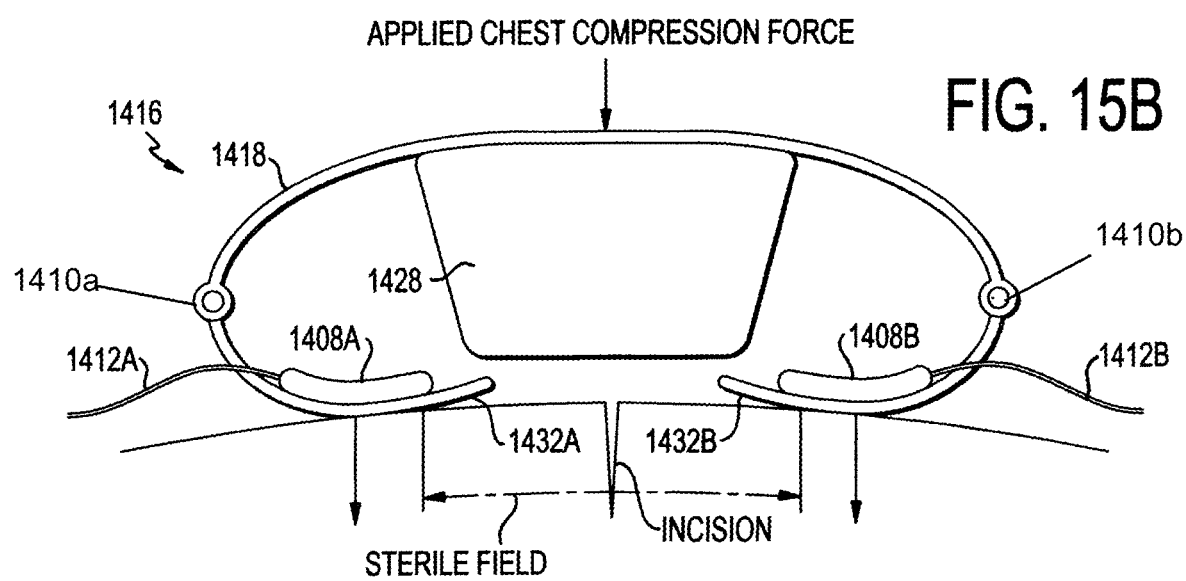
FIG. 15B is a side view of a chest compression assembly, in an example.
Figure 15:
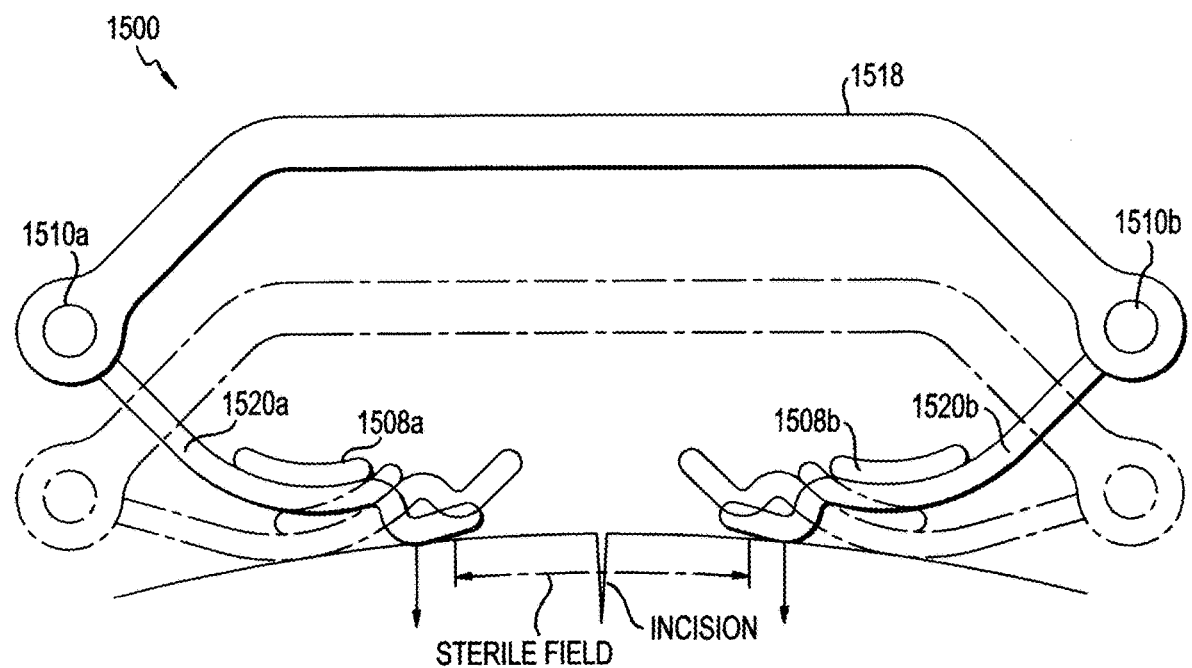
FIGS. 15C and 15D are side views of alternative configurations of a chest compression assembly, in examples.

FIGS. 14 and 15A-B depict various examples chest compression assemblies used to apply chest compressions. In FIG. 14, an example chest compression assembly 1400 includes a wristband 1404, a chest compression sensor 1408, and a lead wire 1412. In this example, the wristband 1404, either fixedly or releasable connected to the chest compression sensor 1408, is used to encircle a hand or wrist of a person providing chest compressions. The wristband 1404 thus places the chest compression sensor 1408 proximate to, and in mechanical communication with, a portion of the body of the person providing chest compressions so that the characteristics of the chest compressions can be measured by the chest compression sensor 1408. In this way, the chest compression sensor 1408 need not be affixed to the thorax of a patient, particularly those patients that have small thoraxes (e.g., infants, children) or patients that have little available area on their thorax for medical devices. Furthermore, because the chest compression sensor 1408 is not in contact with a patient thorax within a sterile field (as shown in FIG. 12), the risk of infection is reduced.

The chest compression sensor 1408 in this example of FIG. 14 also includes at least one gyroscope or at least one three dimensional accelerometer (neither of which are shown) in addition to at least one accelerometer. While the accelerometer measures changes in acceleration that are used to measure the characteristics of the chest compressions, as described above, the gyroscope identifies the orientation of the chest compression sensor 1408 on the wristband 1404. In this way, even if the chest compression sensor 1408 and its corresponding accelerometers are not in a conventional orientation (i.e., not placed in contact with and on top of a patient thorax), the least one gyroscope can identify the orientation so that the data generated by the at least one accelerometer may be analyzed so that the characteristics of the chest compressions are identified.

The chest compression assembly 1416 of FIG. 15A is a structure to which the CPR sensors 1408A and 1408B are attached and includes a central portion 1418, a first portion 1420A and a second portion 1420B. The central portion 1418 is connected to both of the first portion 1420A and the second portion 1420B via corresponding hinges 1410A and 1410B. The hinges may be configured so that upon the application of a downward compression force to the assembly 1416, the first portion 1420A and second portion 1420B may exhibit a tendency to move in toward one another, bringing sides of the incision together, rather than apart. The first portion 1420A and the second portion 1420B can conform to some or all of a spiral that is a continuous function of a polar angle, as is shown. The chest compression assembly 1416 is configured to distribute force applied from a manual CPR compression over an incision to opposing sides of the incision. That is, the chest compression assembly 1416 straddles the incision so that the force of the compressions is not applied to the incision itself or applied with a pressure that re-opens incision or otherwise re-injures the wound caused by the incision. In some instances, the chest compression assembly may be configured such that when a downward chest compression force is applied, the first portion 1420A and the second portion 1420B brings parts of the body located on opposite sides of the sensitive region (e.g., incision, wound) toward one another. Furthermore, the central portion 1418 is configured to fit within a sterile field surrounding the incision (and at least some of a corresponding sensitive region) to reduce the risk of introducing contamination into the sterile field and reduce the risk of further injury to the incision and/or sensitive region. The central portion 1418 in some examples is curved so as to be arcuate having an appropriate radius of curvature and length for its intended purpose. Another benefit of the chest compression assembly 1416 is that it may serve to protect the hands of the person applying chest compressions from injury caused by sternal wires, or other wires, used in the patient.

In the example shown, the chest compression assembly 1416 includes a first portion 1420A configured to come into contact with the patient on a first side of the incision, in this case a transthoracic incision, a second portion 1420B configured to come into contact with the patient on a second side of the transthoracic incision (collectively the "thorax side" of the chest compression assembly 1416), the first side and the second side being on opposite sides of the transthoracic incision, and a central portion 1418 configured to be located over the transthoracic incision (also referred to as "the user side" of the chest compression assembly 1416). As a downward compressive force is applied (as indicated by the arrow in contact with the user side of chest compression assembly 1416, the portions of each of the first portion 1420A and the second portion 1420B in contact with a thorax of a patient receive the pressure applied by the manual CPR compression. This configuration alleviates pressure on the transthoracic incision by distributing force applied from chest compressions over the transthoracic incision to the first side and the second side of the transthoracic incision.

Chest compression sensors 1408A and 1408B are disposed as shown proximate to the thorax and communicate with a controller via lead lines 1412A and 1412B.

In another embodiment, FIG. 15B has a first portion 1432A and a second portion 1432B connected to the central portion 1418 that are less curved than the first portion 1420A and the second portion 1420B shown in FIG. 15A. The chest compression assembly 1416 also includes a resilient pad 1428 disposed to confront a thorax and diffuse pressure applied to the thorax during CPR compressions, thus protecting the transthoracic incision from further injury.

Figure 15D:
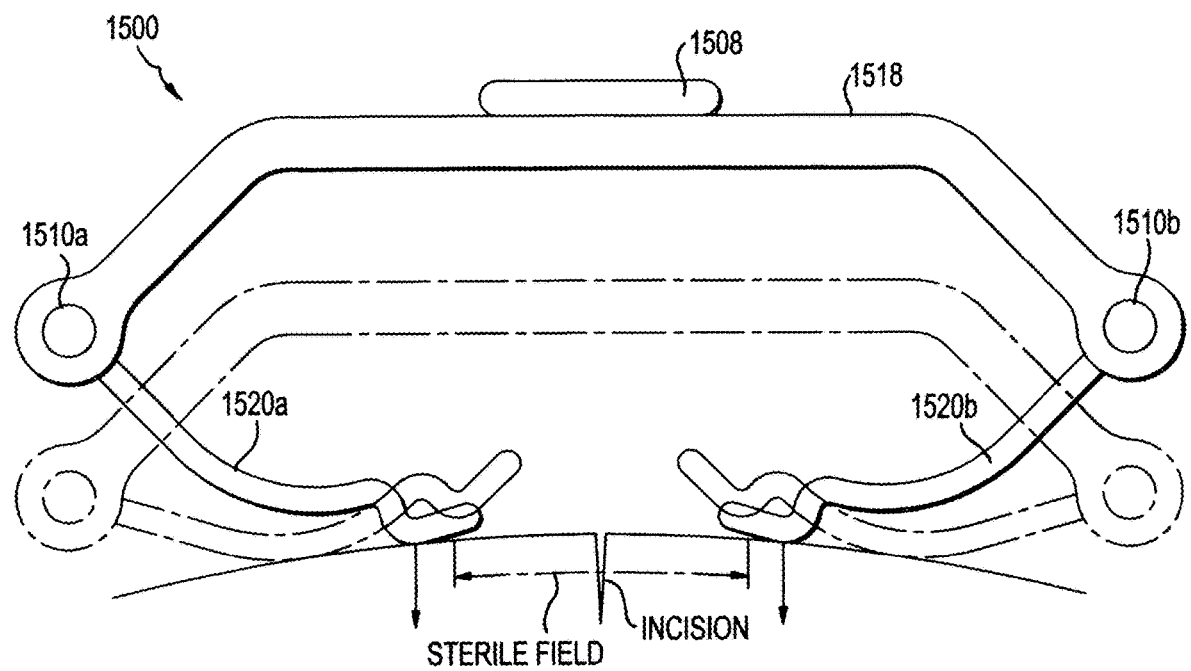

FIGS. 15C and 15D illustrate alternative configurations of chest compression assemblies. Some features of the chest compression sensor 1500, such as its placement on either side of an incision and/or sensitive region, its placement outside a sterile field, the use to transmit an applied chest compression force, and use with a chest compression sensor have been presented above in the context of FIGS. 15A and 15B and need no further explanation.

In FIG. 15C, the chest compression assembly 1500 includes a central portion 1518 connected to a first portion 1520a at a first hinge 1510a and also connected to a second portion 1520b at a second hinge 1510b. The ends of the first portion 1520a and 1520b opposite the corresponding hinge 1510a and 1510b, respectively, can be coated or otherwise include a material that increases a coefficient of friction, for example, as compared to bare metal, so that these end portions are less likely to slide and/or slip along the skin of the thorax when the chest compression assembly 1500 is in use. Such a material may include rubber, silicone, an elastomer, polymer, plastic, or other suitable material that provides a comfortable grip along the surface of the skin.

As with chest compression sensor 1416 shown in FIG. 15A, chest compression sensors 1508a and 1508b are disposed on the first and second portions, respectively, so that a depth and application rate of chest compressions is monitored.

As is also shown in FIG. 15C by the image of the chest compression assembly in dashed lines, an applied chest compression force causes the first and second portions 1508a and 1508b to flex at hinges 1510a and 1510b. As noted above, such flexing of the hinges 1510a and 1510b may provide a slight inward force on either side of the incision as the chest compression assembly is pushed downward, which may be effective to keep the incision closed. In addition, the extent of flexing can be limited by configuring the hinges 1510a and 1510b to include a stopping structure. For example, the chest compression assembly may reach a limit when pushed sufficiently far downward. With this configuration, not only is the applied chest compression force transmitted to an appropriate location on the thorax on either side of a sensitive region, but a component of the applied force may serve to compress the opposing sides of the sensitive region together. This can reduce the risk of chest compressions re-opening an incision.

FIG. 15D shows a chest compression assembly 1500 similar to the example shown in FIG. 15C except that the chest compression sensor 1508 is disposed on the central portion 1518. In this embodiment, when the chest compression assembly reaches its limit (e.g., shown in the dashed lines of FIG. 15D), it behaves as a rigid body where the hinges no longer allow for rotation and the first portion 1520a and second portion 1520b are unable to flex inward. Accordingly, the chest compression sensor 1508 is able to accurately determine the depth of travel of the chest wall, as if the sensor 1508 were placed directly on the first portion 1520a or second portion 1520b.

Figure 16A:
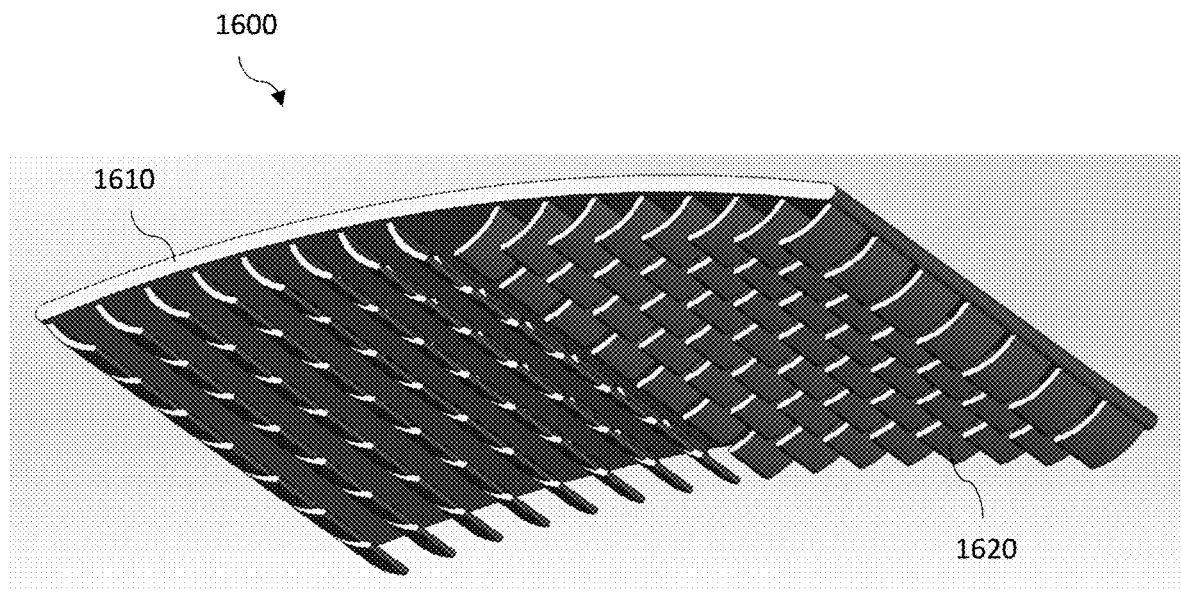
FIG. 16A is a perspective view of a chest compression assembly, in an example.
Figure 16B:
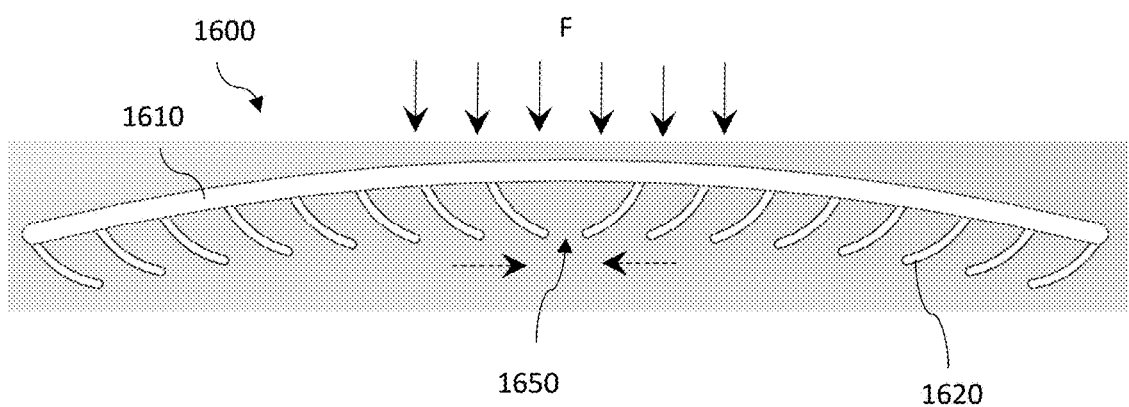
FIG. 16B is a side view of the chest compression assembly of FIG. 16A.

FIGS. 16A and 16B depict another example implementation of a chest compression assembly 1600 that allows for chest compressions to be applied to a patient while limiting the potential for injury or aggravation a sensitive region (e.g., surgical line, wound, etc.). In this embodiment, the chest compression assembly 1600 includes a compression surface 1610 and support members 1620 which extend toward the center of the assembly so as to urge opposing sides adjacent the sensitive region together during the application of chest compressions. The support members 1620 may be provided, for example, as relatively small plastic members that extrude from the bottom of the compression surface 1610 and which are angled toward a central region 1650 of the assembly 1600. The support members 1620 may be formed of any suitable material (e.g., plastic, polymer, elastomer, rubber, amongst others) that is able to transfer force while not leading to injury of the patient when used appropriately.

FIG. 16B shows the chest compression assembly 1600 in use, although the patient surface is not expressly shown here. In this embodiment, a compressive force F (depicted by the solid arrows pointing downward) is applied to the top of the compression surface 1610. While not shown in this figure, the sensitive region of the patient over which chest compressions are to be applied is generally located at the central region 1650 of the assembly 1600, where no actual contact between the compression assembly and sensitive region occurs. The support members 1610 provide protection for the sensitive region, for example, by raising the region at which chest compressions are actually applied and transferring the compression force to the patient thorax surrounding the sensitive region. Because the support members 1610 are angled toward the central region 1650, upon contact with the surface of the patient during a chest compression, similar to other embodiments described herein, the support members 1610 may serve to slightly pinch or push the skin of the patient inward, reducing overall risk of that an incision or other sensitive feature would be opened or otherwise aggravated during the application of chest compressions. The dashed arrows pointing toward the central region 1650 illustrate the effect of the support members 1610 urging the skin of the patient inward.

Figure 17A:
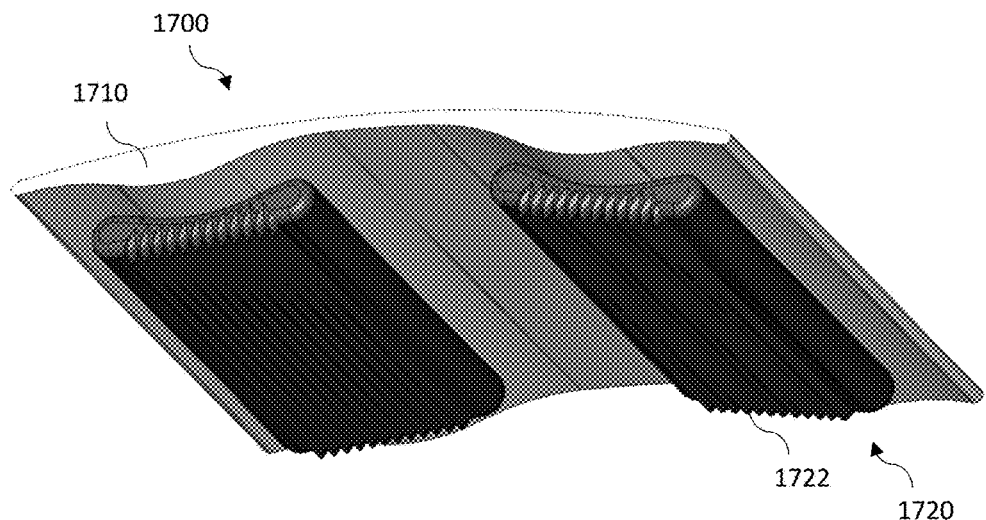
FIG. 17A is a perspective view of a chest compression assembly, in an example.
Figure 17B:
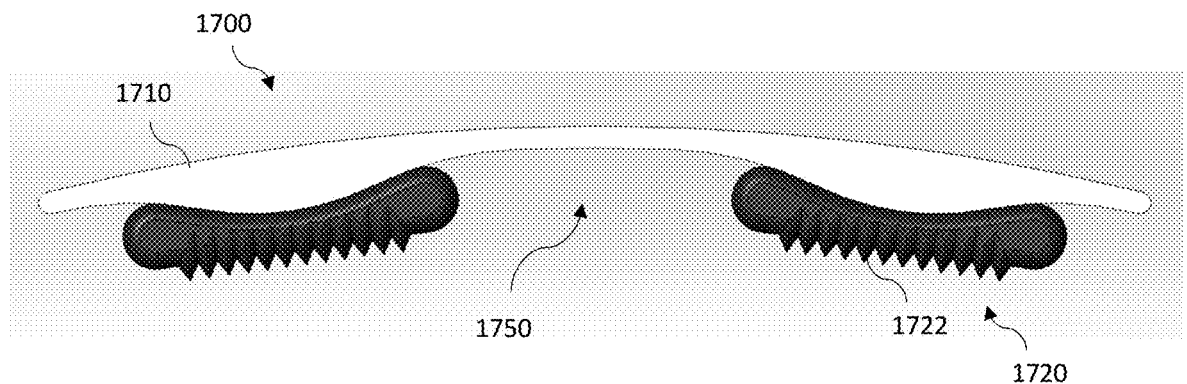
FIG. 17B is a side view of the chest compression assembly of FIG. 17A.
Figure 17C:
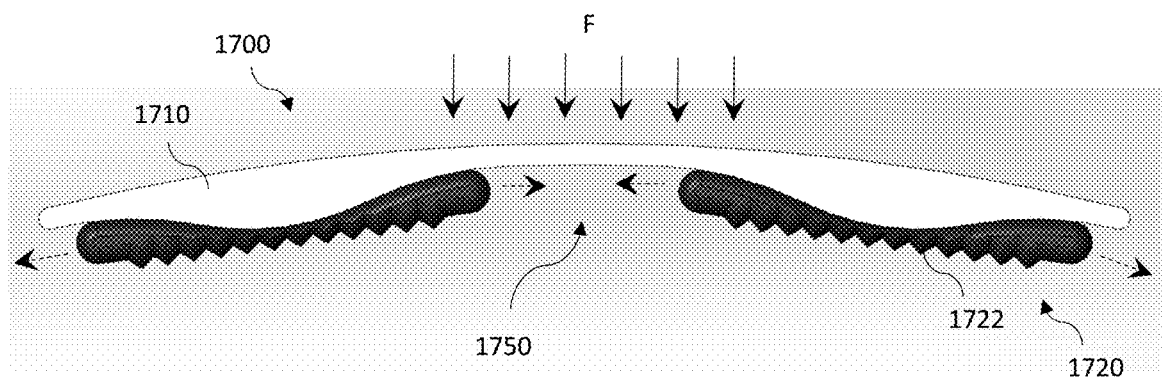
FIG. 17C is a side view of the chest compression assembly of FIG. 17A in a compressed state.

FIGS. 17A-17C illustrate yet another embodiment of a chest compression assembly 1700 for applying chest compressions to the patient while providing protection for a sensitive region over which chest compression are administered. In this embodiment, the chest compression assembly 1700 includes a compression surface 1710 and compressible pads 1720 which may provide a relatively comfortable landing for the chest compression assembly 1700 on the patient. The compressible pads 1720 may be provided on opposite sides of the central region 1750 so that the sensitive region remains relatively undisturbed during chest compressions. The compressible pads 1720 may include an engagement region 1722, for example, provided as texture and/or material suitable for appropriately gripping the skin of the patient upon contact during chest compressions. Further, the compressible pads 1720 may be deformable in a manner that causes the side edges of the pads 1720 to squeeze outward as the pads are compressed downward. The compressible pads 1720 may be formed of an appropriate material, such as plastic, polymer, elastomer, rubber, etc.

FIGS. 17B-17C depict the chest compression assembly 1700 in use, although the patient surface is not expressly shown in these figures. In this example, FIG. 17B shows the chest compression assembly 1700 in a resting state where no compressive force is applied thereto. FIG. 17C shows a compressive force F (depicted by the solid arrows pointing downward) applied to the top surface of the compression surface 1710. While not expressly shown here, the sensitive region of the patient over which chest compressions are to be applied is generally located at the central region 1750 of the assembly 1700, without being in actual contact with the assembly 1700. The chest compression assembly 1700 is constructed to protect the sensitive region of the patient, for example, by providing the compressible pads 1720 to raise the surface at which chest compressions are applied. The compressible pads 1720 also transfer compression force applied to compression surface 1710 to the patient thorax around the sensitive region. As further shown in FIG. 17C, the application of compressive force F causes the compressible pads 1720 to be squeezed and, hence, deform slightly outward, as illustrated by the dashed arrows. In some cases, particularly in instances where the engagement regions 1722 are able to effectively grip the skin of the patient, this deformation of the compressible pads 1720 gently pushes the skin of the patient inward so as to reduce the chances of opening or aggravating an incision or other sensitive feature during the application of chest compressions.

What is claimed is:

1. A defibrillation electrode assembly for use in providing resuscitative treatment to a patient, comprising:
    an individual therapy pad comprising
        a non-conductive substrate,
        an electrically conductive layer in contact with the non-conductive substrate and configured to distribute a defibrillation current,
        a single terminal in electrical communication with the electrically conductive layer, and
        a lead wire connected to the terminal, the lead wire and the terminal placing the electrically conductive layer in electrical contact with a power source,
    wherein the individual therapy pad has a length to width aspect ratio of equal to or greater than 3:1 and less than or equal to 30:1.

2. The defibrillation electrode assembly of claim 1, wherein the length to width aspect ratio of the individual therapy pad is from 5:1 to 20:1.

3. The defibrillation electrode assembly of claim 1, further comprising a conductive gel in contact with the electrically conductive layer.

4. The defibrillation electrode assembly of claim 1, wherein the individual therapy pad further comprises a perimeter edge, and further wherein the perimeter edge has a curved edge from a point at the perimeter edge to an end of at least one straight line to form a rounded corner.

5. The defibrillation electrode assembly of claim 1, wherein the individual therapy pad further comprises a pattern disposed on the individual therapy pad, the pattern depicting at least one boundary at which a first portion of the individual therapy pad having the single terminal is configured to be separable from a second portion of the individual therapy pad.

6. The defibrillation electrode assembly of claim 5, wherein the pattern comprises a plurality of approximately parallel lines defining a plurality of elongated members.

7. The defibrillation electrode assembly of claim 5, wherein the pattern comprises perforations or thinned regions defined by at least the non-conductive substrate and the electrically conductive layer.

8. The defibrillation electrode assembly of claim 1, further comprising an adhering material configured to transmit the defibrillation current from the electrically conductive layer to the patient and configured to couple the individual therapy pad to a sensitive region of the patient, wherein the adhering material exhibits a peel strength of between 0.01 lbs and 0.5 lbs at a pull rate of 10 inches/min.

9. The defibrillation electrode assembly of claim 1, further comprising:
    a sterile pouch defining a sterile space therein; and
    a chest compression sensor within the sterile space.

10. A defibrillation electrode assembly for use in providing resuscitative treatment to a patient, comprising:
    a therapy pad comprising:
        a non-conductive substrate, and an electrically conductive layer in contact with the non-conductive substrate and configured to distribute a defibrillation current;
a sterile pouch defining a sterile space therein; and
a chest compression sensor removably within the sterile space of the sterile pouch.

11. The defibrillation electrode assembly of claim 10, further comprising a chest compression sensor wherein the chest compression sensor comprises at least one of an accelerometer and a gyroscope.

12. The defibrillation electrode assembly of claim 11, wherein the chest compression sensor is configured to be placed at a position away from a sternum during administration of chest compressions.

13. The defibrillation electrode assembly of claim 11, wherein the chest compression sensor is configured to be placed over a sternum during administration of chest compressions.

14. The defibrillation electrode assembly of claim 11, wherein the sterile pouch with the chest compression sensor therein is configured to be disposed within a sterile field prior to use, the sterile pouch preventing exposure of the chest compression sensor within a sterile field associated with a transthoracic incision.

15. The defibrillation electrode assembly of claim 10, further comprising a conductive gel in contact with the electrically conductive layer.

16. The defibrillation electrode assembly of claim 10, further comprising:
an electrical conductor connected to the chest compression sensor, the electrical conductor configured to transmit at least one of acceleration data and orientation data from the chest compression sensor to a processor.

17. The defibrillation electrode assembly of claim 16, wherein the sterile pouch is configured to encapsulate the chest compression sensor and at least a portion of the electrical conductor.

18. The defibrillation electrode assembly of claim 16, wherein the electrical conductor comprises a ribbon cable.

19. The defibrillation electrode assembly of claim 10, further comprising a pattern disposed on the therapy pad, the pattern depicting at least one boundary at which a first portion of the therapy pad is separable from a second portion of therapy pad, the first portion and the second portion each including a portion of the electrically conductive layer.

20. The defibrillation electrode assembly of claim 10, wherein the sterile pouch includes a sealed closure for maintaining the chest compression sensor within the sterile space.

21. The defibrillation electrode assembly of claim 20, wherein opening of the sealed closure exposes the chest compression sensor to a surrounding environment.

22. The defibrillation electrode assembly of claim 10, further comprising a pattern disposed on the therapy pad, the pattern depicting at least one boundary at which a first portion of the therapy pad is configured to be separable from a second portion of the therapy pad, the first portion and the second portion each including a portion of the electrically conductive layer.

23. The defibrillation electrode assembly of claim 10, wherein the therapy pad has a length to width aspect ratio of greater than or equal to 3:1 and less than or equal to 30:1.

24. The defibrillation electrode assembly of claim 10, further comprising an adhering material configured to transmit the defibrillation current from the electrically conductive layer to the patient and configured to couple the therapy pad to a sensitive region of the patient, wherein the adhering material exhibits a peel strength of between 0.01 lbs and 0.5 lbs at a pull rate of 10 inches/min.

* * * * *